(12) United States Patent
DiMaggio et al.

(10) Patent No.: US 8,930,206 B2
(45) Date of Patent: Jan. 6, 2015

(54) MEDICAL CARE ADMINISTRATION SYSTEM AND METHOD

(75) Inventors: John DiMaggio, Powell, OH (US); Paul Guth, New Albany, OH (US); Timothy Friar, Sunbury, OH (US); Robert Kerr, Eldersburg, MD (US); Jerome Romick, New Albany, OH (US); Michael Russo, Woodbine, MD (US); Bonnie Spiers, Westerville, OH (US); Daniel Drasin, Columbia, MD (US); John Allen Stutz, Leawood, KS (US)

(73) Assignee: Remedi Technology Holdings, LLC, Baltimore, MD (US)

( * ) Notice: Subject to any disclaimer, the term of this patent is extended or adjusted under 35 U.S.C. 154(b) by 1901 days.

(21) Appl. No.: 11/788,603

(22) Filed: Apr. 20, 2007
(Under 37 CFR 1.47)

(65) Prior Publication Data
US 2008/0010089 A1    Jan. 10, 2008

Related U.S. Application Data

(60) Provisional application No. 60/745,314, filed on Apr. 21, 2006.

(51) Int. Cl.
*G06Q 50/00* (2012.01)
*G06Q 10/00* (2012.01)
*G06F 19/00* (2011.01)
*G06Q 50/22* (2012.01)

(52) U.S. Cl.
CPC .............. *G06F 19/327* (2013.01); *G06Q 50/22* (2013.01)
USPC ........................................... 705/2

(58) Field of Classification Search
USPC .................... 705/2–3, 8; 70/2–3, 8
See application file for complete search history.

(56) References Cited

U.S. PATENT DOCUMENTS

| | | |
|---|---|---|
| 4,338,083 A | 7/1982 | Andrae |
| 4,766,542 A | 8/1988 | Pilarczyk |
| 5,322,406 A | 6/1994 | Pippin et al. |
| 5,623,242 A | 4/1997 | Dawson, Jr. et al. |
| 5,737,539 A | 4/1998 | Edelson et al. |
| 5,758,095 A | 5/1998 | Albaum et al. |
| 5,801,755 A | 9/1998 | Echerer |
| 5,907,493 A | 5/1999 | Boyer et al. |
| 5,991,731 A | 11/1999 | Colon et al. |

(Continued)

OTHER PUBLICATIONS

PCT Application No. PCT/US07/09600, International Search Report and the Written Opinion, Apr. 8, 2008, 17 pages.

*Primary Examiner* — Minnah Seoh
(74) *Attorney, Agent, or Firm* — Oblon, Spivak, McClelland, Maier & Neustadt, L.L.P.

(57) ABSTRACT

A medical care administration system that continuously provides accurate identifications of what medical care orders are due for administration in a medical care facility. The system uses a services oriented architecture to provide an interface with a pharmacy. The architecture provides message formats and respective data definitions in a web services descriptive language. Thus, data relating to medical care orders may be stored in a relational database in normative format of definitions that is independent of known pharmacy codes and definitions. With the system, all written orders are sent to a pharmacy by facsimile copy and returned to the care facility in electronic form for comparison with the written order. The system further provides a user interface that leads a person through an administration process and simplifies creation of an electronic administration record.

42 Claims, 50 Drawing Sheets

(56) References Cited

U.S. PATENT DOCUMENTS

| | | | |
|---|---|---|---|
| 6,157,381 A | 12/2000 | Bates et al. |
| 6,202,923 B1 | 3/2001 | Boyer et al. |
| 6,421,650 B1 | 7/2002 | Goetz et al. |
| 6,438,451 B1 | 8/2002 | Lion |
| 6,529,801 B1 | 3/2003 | Rosenblum |
| 6,564,121 B1 | 5/2003 | Wallace et al. |
| 6,611,806 B1 | 8/2003 | Harvey |
| 6,636,780 B1 | 10/2003 | Haitin et al. |
| 6,640,212 B1 | 10/2003 | Rosse |
| 6,654,724 B1 | 11/2003 | Rubin et al. |
| 6,670,885 B2 | 12/2003 | Kosaka |
| 6,697,704 B2 | 2/2004 | Rosenblum |
| 6,711,460 B1 | 3/2004 | Reese |
| 6,766,218 B2 | 7/2004 | Rosenblum |
| 6,859,780 B1 | 2/2005 | Cunningham |
| 6,892,941 B2 | 5/2005 | Rosenblum |
| 6,935,560 B2 | 8/2005 | Andreasson et al. |
| 6,983,579 B2 | 1/2006 | Rice et al. |
| 6,988,075 B1 | 1/2006 | Hacker |
| 7,006,893 B2 | 2/2006 | Hart et al. |
| 7,155,306 B2 | 12/2006 | Haitin et al. |
| 7,185,315 B2 | 2/2007 | Sharp et al. |
| 2001/0025246 A1 | 9/2001 | Haines et al. |
| 2001/0034613 A1 | 10/2001 | Rubsamen |
| 2001/0044731 A1 | 11/2001 | Coffman et al. |
| 2002/0016718 A1* | 2/2002 | Rothschild et al. | 705/2 |
| 2002/0042725 A1 | 4/2002 | Mayaud |
| 2002/0042726 A1 | 4/2002 | Mayaud |
| 2002/0052760 A1 | 5/2002 | Munoz et al. |
| 2002/0052762 A1 | 5/2002 | Kobylevsky et al. |
| 2002/0069088 A1 | 6/2002 | Berg |
| 2002/0143434 A1 | 10/2002 | Greeven et al. |
| 2002/0143582 A1 | 10/2002 | Neuman et al. |
| 2002/0165736 A1 | 11/2002 | Tolle et al. |
| 2002/0188467 A1 | 12/2002 | Eke |
| 2003/0018495 A1 | 1/2003 | Sussman |
| 2003/0074222 A1* | 4/2003 | Rosow et al. | 705/2 |
| 2003/0088333 A1 | 5/2003 | Liff et al. |
| 2003/0093295 A1 | 5/2003 | Lilly et al. |
| 2003/0120384 A1 | 6/2003 | Haitin et al. |
| 2003/0125837 A1 | 7/2003 | Walace et al. |
| 2003/0158755 A1 | 8/2003 | Neuman |
| 2003/0164401 A1 | 9/2003 | Andreasson et al. |
| 2003/0167190 A1 | 9/2003 | Rincavage et al. |
| 2003/0177033 A1 | 9/2003 | Park et al. |
| 2003/0212577 A1 | 11/2003 | Nichtberger |
| 2003/0225627 A1 | 12/2003 | Mast |
| 2004/0006490 A1 | 1/2004 | Gingrich et al. |
| 2004/0019567 A1 | 1/2004 | Herceg et al. |
| 2004/0024616 A1 | 2/2004 | Spector et al. |
| 2004/0046020 A1 | 3/2004 | Andreasson et al. |
| 2004/0078231 A1 | 4/2004 | Wilkes et al. |
| 2004/0122712 A1 | 6/2004 | Hill, Sr. et al. |
| 2004/0128162 A1 | 7/2004 | Schlotterbeck et al. |
| 2004/0138921 A1 | 7/2004 | Broussard et al. |
| 2004/0148198 A1 | 7/2004 | Kalies |
| 2004/0172162 A1 | 9/2004 | Bonney et al. |
| 2004/0172283 A1 | 9/2004 | Vanderveen et al. |
| 2004/0172289 A1 | 9/2004 | Kozic et al. |
| 2004/0172295 A1 | 9/2004 | Dahlin et al. |
| 2004/0215369 A1 | 10/2004 | Rosenblum |
| 2004/0232219 A1 | 11/2004 | Fowler |
| 2004/0238631 A1 | 12/2004 | Andreasson et al. |
| 2005/0010448 A1 | 1/2005 | Mattera |
| 2005/0033606 A1 | 2/2005 | Miller |
| 2005/0038558 A1 | 2/2005 | Keene |
| 2005/0049746 A1 | 3/2005 | Rosenblum |
| 2005/0055244 A1 | 3/2005 | Mullan et al. |
| 2005/0060200 A1 | 3/2005 | Kobylevsky et al. |
| 2005/0080651 A1 | 4/2005 | Morrison et al. |
| 2005/0086081 A1 | 4/2005 | Brock-Fisher |
| 2005/0102163 A1 | 5/2005 | Coughlin |
| 2005/0107914 A1 | 5/2005 | Engleson et al. |
| 2005/0108050 A1* | 5/2005 | Knapheide | 705/2 |
| 2005/0108053 A1 | 5/2005 | Jones, Jr. |
| 2005/0119788 A1 | 6/2005 | Engleson et al. |
| 2005/0131579 A1 | 6/2005 | Andreasson et al. |
| 2005/0177392 A1 | 8/2005 | Domashnev |
| 2005/0182656 A1 | 8/2005 | Morey |
| 2005/0182662 A1 | 8/2005 | Pierce |
| 2005/0187789 A1 | 8/2005 | Hatlestad et al. |
| 2005/0187791 A1 | 8/2005 | DiMaggio et al. |
| 2005/0209879 A1 | 9/2005 | Chalmers |
| 2005/0216199 A1 | 9/2005 | Banet |
| 2005/0261938 A1 | 11/2005 | Silverbrook et al. |
| 2005/0261940 A1 | 11/2005 | Gay et al. |
| 2006/0032918 A1 | 2/2006 | Andreasson et al. |
| 2006/0053036 A1 | 3/2006 | Coffman et al. |
| 2006/0054682 A1 | 3/2006 | de la Huerga |
| 2006/0060645 A1 | 3/2006 | Udaka et al. |
| 2006/0065713 A1 | 3/2006 | Kingery |
| 2006/0065726 A1 | 3/2006 | Andreasson et al. |

* cited by examiner

Data Definitions for Medication Order Object

| Data Element | Type & Size | Description | Sample Data |
|---|---|---|---|
| ORDER_ IDENTITY_ KEY | String | The pharmacy system assigned unique order identity key. In some systems this may be the initial Rx#. It is critical that although Rx numbers may change month-to-month for billing purposes (think unit dose systems), that this identity key stay constant for all refills generated for the initial Rx. This key is used as a grouping key within eMAR to associate different Rx numbers (and bar code scan codes) to the same order. | R0343433 |
| ORDER_ CHANGE_ DATE | dateTime | The date that the pharmacy system created the underlying transaction (new, change, refill). This information is necessary to keep track of changes (including refills) to an order. | 01/01/2006 15:00:15 |
| ORDER_ ORDERING_ PHYSICIAN | String | Foreign key that identifies the ordering physician with the PHYSICIAN_IDENTITY_KEY attribute of the physician object (see Appendix 7) | 00043433 |
| ORDER_ RESIDENT | String | Foreign key that identifies the resident with the RESIDENT_IDENTITY_KEY attribute of the resident object (see Appendix 6) | 000034344 |
| ORDER_ CURRENT_ RX_NUM | String | The Rx number associated with the new order. For new orders, this data element and the ORDER_IDENTITY_KEY may be the same. | R0343433 |
| ORDER_ START_ DATE | dateTime | Order start date in MM/DD/YYYY hh:nn:mm format. It is assumed that the start date is the first date of administration. If Pharmacy doesn't support time values use 00:00:01. For all standing orders default the latest Admission date. | 01/02/2006 15:34:34 |
| ORDER_ END_ DATE | dateTime | Order end date in MM/DD/YYYY hh:nn:mm format. If there is no end date (which is typical in long term care), then the Pharmacy Interface Gateway must send in a NULL token which will be interpreted as the order that will stay active until it is discontinued. Obviously, for duration orders this value must be provided. It is assumed that the end date is the last date of administration (not the day after the last date of administration). | 00/00/0000 14:34:45 |

FIG. 3A

Data Definitions for Medication Order Object

| Data Element | Type & Size | Description | Sample Data |
|---|---|---|---|
| ORDER_IS_CHART_ONLY | boolean | Flag to indicate if this order is a "chart only" order meaning there will be no meds sent for this order. Valid answers are ? oolean: true or false. | False |
| ORDER_IS_HOUSE_STOCK | boolean | Flag to indicate if this order is a "house stock" order meaning there will be no meds sent for this order. Valid answers are ? oolean: true or false. | False |
| ORDER_IS_SPLIT_SIG | boolean | A flag to indicate that the order is a split-sig order (i.e. two sets of frequencies, pass times, qty to administer). Please note that frequency, pass times, qty administer, etc. will be ignored for split sig orders and treated "passively" for eMAR Release 1. This will make the order always present on the eMAR (internally called 'Unschedulable') and would require a complete DC and replacing of the order to change. Artromick feels this is the safest way to handle these types of complex orders due to semantic differences between different pharmacy systems. | True |
| ORDER_DRUG_NAME | String | The drug name as it appears on the Rx label, including substitution information.<br><br>Be sure when sending this object for refill transactions that this attribute is updated with the proper value. | CELEXA 10MG TABLET SUB LEXIPRO |
| ORDER_NDC_CODE | String | NDC code of the drug corresponding with ORDER_DRUG_NAME. If the drug is a compound, send the word "COMPOUND" rather than the NDC of the most expensive ingredient.<br><br>Be sure when sending this object for refill transactions that this attribute is updated with the proper value. | 00343433433 |
| ORDER_IS_COMPOUND | boolean | Flag to indicate if the order is supplied by a compound. Valid answers are ? oolean: true or false. | False |
| ORDER_IS_IV_COMPOUND | boolean | Flag to indicate if the order is supplied by an IV compound. Valid answers are ? oolean: true or false. | False |
| ORDER_DEA_CLASS | String | Indicates the drug DEA class. Valid answers are 0,1,2,3,4 & 5. DEA Class of 2 will be specially called out by the interface and shown in Roman Numeral | 0 |

FIG. 3B

Data Definitions for Medication Order Object

| Data Element | Type & Size | Description | Sample Data |
|---|---|---|---|
| ORDER_IS_PSHYCO | boolean | Flag to indicate if the order is considered a psychoactive medication. Valid answers are ?oolean: true or false. | True |
| ORDER_INSTR_TEXT | String | The total order instructions sans the drug name as it would be printed on the MAR. If that is not possible, then provide the text that printed on the Rx label. This is to compensate for different levels of expanded text (i.e. MAR could be full expanded text, label could be shorter version of expanded text or code). | Give 1 Tablet by Mouth Every Day for Pain |
| ORDER_FREQ_CODE | String | The frequency code indicating frequency of administration. If provided, these codes will be matched up to a standard set of codes that are mapped within eMAR to the specific pharmacy. If not known send over the token of 'REVIEW' which will prompt the nurse to make the scheduling decision  For split sig orders this field will be ignored by eMAR. | BID |
| ORDER_IS_PASS_TIME_OVERRIDE | boolean | A flag to indicate that ORDER_PASS_TIMES were overridden by data entry at the time the order was placed (ignoring the default pass times for the frequency setup for that facility and/or nursing station). Valid answers are ?oolean: true or false. | False |
| ORDER_REPEAT_EVERY_X_DAYS | String | Indicates interval of the day administration. The default value is 1 which means "every day". 2 means every other day, 3 every 3 days, etc. | 1 |
| ORDER_IS_PRN | boolean | Flag to indicate if the order is PRN. Valid answers are boolean: true or false. | False |
| ORDER_ROUTE | String | Order route of administration as finally packaged. | IV |

FIG. 3C

| \multicolumn{4}{|l|}{Data Definitions for Non-Medication Order Object} |
|---|---|---|---|

| Data Element | Type & Size | Description | Sample Data |
|---|---|---|---|
| ORDER_ IDENTITY_ KEY | String | The pharmacy system assigned unique order identity key. | 3432233 |
| ORDER_ CHANGE_ DATE | dateTime | The date that the pharmacy system created the underlying transaction (new, change). This information is necessary to keep track of changes to an order. | 01/01/2006 15:00:15 |
| ORDER_ ORDERING_ PHYSICIAN | String | Foreign key that identifies the ordering physician with the PHYSICIAN_IDENTITY_KEY attribute of the physician object (see Appendix 7) | 00043433 |
| ORDER_ RESIDENT | String | Foreign key that identifies the resident with the RESIDENT_IDENTITY_KEY attribute of the resident object (see Appendix 6) | 000034344 |
| ORDER_ START_ DATE | dateTime | Order start date in MM/DD/YYYY format. Time of 00:00:00 will be interpreted as "beginning of day." | 01/02/2006 15:45:34 |
| ORDER_ END_ DATE | dateTime | Order end date in MM/DD/YYYY format. If there is no end date (which is typical in long term care), then the Pharmacy Interface Gateway must send NULL which will be interpreted as the order that will stay active until it is discontinued. Obviously, for duration orders this value must be provided. It is assumed that the end date is the last date of activity (not the day after the last date of activity). | 00/00/0000 15:43:45 |
| ORDER_ IS_SPLIT_ SIG | boolean | A flag to indicate that the order is a split-sig order (i.e. two sets of frequencies, pass times, qty to administer). Please note that frequency, pass times, qty administer, etc. will be ignored for split sig orders and treated "passively" for eMAR Release1. Artromick feels this is the safest way to handle these types of complex orders due to semantic differences between different pharmacy systems. Valid answers are boolean: true or false. | false |

FIG. 3D

| Data Definitions for Non-Medication Order Object ||||
| Data Element | Type & Size | Description | Sample Data |
| --- | --- | --- | --- |
| ORDER_ INSTR_ TEXT | String | The total order instructions sans the drug name as it would be printed on the MAR. If that is not possible, then provide the text that printed on the Rx label. This is to compensate for different levels of expanded text (i.e. MAR could be full expanded text, label could be shorter version of expanded text or code). | Flush IV Catheter Daily |
| ORDER_ USE_ ADMIN_ EVENT_ OVERRIDES | boolean | Flag to indicate if administration event overrides are used in place of order pass time values within this object. See the section "Data Specification for Administration Event Overrides" for more details on which data elements get overridden and ignored in this object. Valid answers are boolean: true or false. | false |
| ORDER_ IS_PASS_ TIME_ OVERRIDE | boolean | A flag to indicate that ORDER_PASS_TIMES were overridden by data entry at the time the order was placed (ignoring the default pass times for the frequency setup for that facility and/or nursing station). Valid answers are boolean: true or false. | false |
| ORDER_ REPEAT_ EVERY_ X_DAYS | String | Indicates how often the pass times occurs. The default value is 1 which means "every day". 2 means every other day, 3 every 3 days, etc. | 1 |
| ORDER_IS_ PRN | boolean | Flag to indicate if the order is PRN. Valid answers are boolean: true or false. | false |

FIG. 3E

Data Definitions for Discontinue & Void Orders Object

| Data Element | Type & Size | Description | Sample Data |
|---|---|---|---|
| ORDER_ IDENTITY_ KEY | String | The pharmacy system assigned unique order identity key corresponding to the order that was discontinued or void. | 3432233 |
| ORDER_ DC_ DATE | dateTime | Order DC date. Can be "null" to represent an reverse DC. Time portion of this dateTime will be ignored.<br><br>We highly recommend that if at all possible, that the pharmacy system do not allow an un-DC transaction since it will negatively impact the point of care eMAR system because once that order stops at the nursing home, it will not be turned back on. | 03/12/2006 |

FIG. 3F

Data Definitions for Resident Demographics Object

| Data Element | Type & Size | Description | Sample Data |
|---|---|---|---|
| RESIDENT_IDENTITY_KEY | String | The pharmacy system assigned unique resident identity key. This key must be unique for all residents and can never be changed by a human. Additionally, within a chain of pharmacies that may service the same facility, this key must be unique across the chain of pharmacies. This is a critical data element that links residents to orders within eMAR. | 000034344 |
| RESIDENT_FIRST_NAME | String | Resident's first name. | Mike |
| RESIDENT_LAST_NAME | String | Resident's last name. | Forester |
| RESIDENT_FACILITY_ID | String | The unique facility id that the resident resides in. This must match up with the facility setup tables within eMAR otherwise the transaction cannot be accepted. This id must be unique within the pharmacy system, or within a group of pharmacy systems servicing a facility chain. | 23 |
| RESIDENT_NURSING_STATION_ID | String | Identifies the nursing station the resident is assigned to. This value must match up with the facility setup tables within eMAR. This id must be unique across all nursing stations defined in the facility specified in RESIDENT_FACILITY_ID | 1 or EAST |
| RESIDENT_IS_CRUSH_ALL_MEDS | boolean | A flag to indicate if the resident requires crushing of meds. Valid answers are boolean: true or false. | true |
| RESIDENT_ATTENDING_PHYSICIAN | String | Foreign key that identifies the resident's attending physician with the PHYSICIAN_IDENTITY_KEY attribute of the physician object (see Appendix 7) | 00043433 |
| RESIDENT_IS_ENTERAL_FEEDER | boolean | A flag to indicate if the resident is an enteral feeder. Valid answers are boolean: true or false. | true |
| RESIDENT_ALLERGIES | String | Free form text listing of drug and other allergies. Valid answers are either text containing allergy description, or, the words "NO KNOWN ALLERGIES" | ASPIRIN, SULFA DRUGS |

FIG. 3G

Data Definitions for Physician Demographics Object

| Data Element | Type & Size | Description | Sample Data |
|---|---|---|---|
| PHYSICIAN_ IDENTITY_ KEY | String | The pharmacy system assigned unique physician identity key. This key must be unique for all physicians and can never be changed by a human. Additionally, within a chain of pharmacies that may service the same facility, this key must be unique across the chain of pharmacies. This is a critical data element that links physicians to residents and orders within eMAR. | 00043433 |
| PHYSICIAN_ FIRST_ NAME | String | Physician's first name. | Mary |
| PHYSICIAN_ LAST_ NAME | String | Physician's last name. | Moore |

FIG. 3H

Data Definitions for Administration Event Overrides Object

| Data Element | Type & Size | Description | Sample Data |
|---|---|---|---|
| ADMIN_ ORDER_ IDENTITY_ KEY | String | Foreign key that identifies the order that the administration event overrides apply to (links to ORDER_IDENTITY_KEY). | R0343433 |

```
select count(order_id) from select
  now
  , start_int
  , stop_int
  , case repeat_months
      when 0 then trunc((now - start_int)/(repeat_hours/24))
      else trunc(months_between(now, start_int))
      end as start_count
  , case repeat_months
      when 0 then trunc((now - stop_int)/(repeat_hours/24))
      else trunc(months_between(now, stop_int))
      end as end_count
  , repeat_hours
  , order_id
from select
  START_CALENDAR
  , now
  , cast((START_CALENDAR + (start_offset/1440)) as date) as start_int
  , cast((START_CALENDAR + (end_offset/1440)) as date) as stop_int
  , repeat_hours
  , repeat_months
  , order_id
from
(select FREQ_ELEMENT.START_CALENDAR
     , FREQ_DEFN_ELEMENT.START_OFFSET
     , FREQ_DEFN_ELEMENT.END_OFFSET
     , FREQ_DEFN_ELEMENT.REPEAT_HOURS
     , FREQ_DEFN_ELEMENT.REPEAT_MONTHS
     , SYSDATE as now -- now
     , freq_element.ORDER_ID
from
  FREQ_DEFN
  , FREQ_ELEMENT
  , FREQ_DEFN_ELEMENT
  , orders
  where FREQ_DEFN.dsid = FREQ_DEFN_ELEMENT.freq_defn_id
  and FREQ_ELEMENT.freq_defn_id = FREQ_DEFN_ELEMENT.dsid
  and orders.dsid = freq_element.ORDER_ID
  and freq_element.start_calendar < SYSDATE  -- "now"
  and (not (FREQ_ELEMENT.stop_offset between to_date('01/01/0001', 'MM/DD/YYYY') and to_date('01/01/4001', 'MM/DD/YYYY'))
      or (FREQ_ELEMENT.stop_offset > SYSDATE)) -- "now"
  and orders.order_status = 2
))) fes
where fes.start_count != end_count
```

FIG. 9

$o \in Orders$ $fe_1 \ldots fe_n \in FrequencyElements$ $fde_1 \ldots fde_n \in FrequencyDefinitionElements$ $fd \in FrequencyDefinitions$ Assume that Orders, FrequencyElements, and FrequencyDefintionElements have the following functions defined for all members.

Orders:
- frequencyDefinition(o)
- startDate(o)

FrequencyElements:
- frequencyDefinitionElement(fe)
- order(fe)
- startOffset(fe)

FrequencyDefinitionElement
- frequency(fde)
- start(fde)
- stop(fde)
- repeat(fde)

Such that
$$\forall fe_i : order(fe_i) = o$$
$$\forall fe_i : frequencyDefinitionElement(fe_i) = fde_i$$
$$frequencyDefinition(o) = fd$$
$$\forall fde_i : frequency(fde_i) = fd$$

In addition, we define the following:

$effectiveStart(fe) = startDate(order(fe)) + startOffset(fe)$

We define n different pair of series (the same as the cardinality of FrequencyElements and FrequencyDefinitionElements subsets that we are considering). We can now determine the $m^{th}$ element of these "administration series" – termed "administrative start series" and "administrative end series" – as follows:

$adm\_start_{n,m}$ $= effectiveStart(fe_n)$ $+ (repeat(frequencyDefinitionElement(fe_n)) \cdot m)$ $+ start(frequencyDefinitionElement(fe_n))$ And

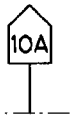

And
$$adm\_end_{n,m}$$
$$= effectiveStart(fe_n)$$
$$+ (repeat(frequencyDefinitionElement(fe_n)) \cdot m)$$
$$+ stop(frequencyDefinitionElement(fe_n))$$

In addition, when the following
$$\forall fe_i : startOffset(fe_i) = startOffset(fe_1)$$
$$\forall fde_i : repeat(fde_i) = repeat(fde_1)$$

Then we can consider the n different administration series to be "correlated" – i.e. the $k^{th}$ element of all series occur before the $k+1^{th}$ element of all series and if the $l^{th}$ element of some series occurs before the $l^{th}$ element of another series, then $j^{th}$ element of that series will occur before the $j^{th}$ element of the other series. This means that we can determine the $m^{th}$ element of the correlated series of all administrative series as follows:

$$seriesChoice(m) = remainder(\frac{m-1}{n})$$
$$seriesCounter(m) = floor(m-1) + 1$$
$$adm\_start_m = adm\_start_{seriesChoice(m),seriesCounter(m)}$$

And
$$seriesChoice(m) = remainder(\frac{m-1}{n})$$
$$seriesCounter(m) = floor(m-1) + 1$$
$$adm\_end_m = adm\_end_{seriesChoice(m),seriesCounter(m)}$$

In addition, we can determine if a given time is in an "administrative window" as follows.

First we define a time, T, as being in an administrative window if and only if
$$adm\_start_m \leq T \text{ and } adm\_end_m \geq T \text{ for some } m.$$

Thus we can determine if T is within an administrative window if and only if
$$\exists n : floor(\frac{T - (effectiveStart(fe_n) + start(fde_n))}{repeat}) - floor(\frac{T - (effectiveStart(fe_n) + stop(fde_n))}{repeat}) \neq 0$$

FIG. 10B

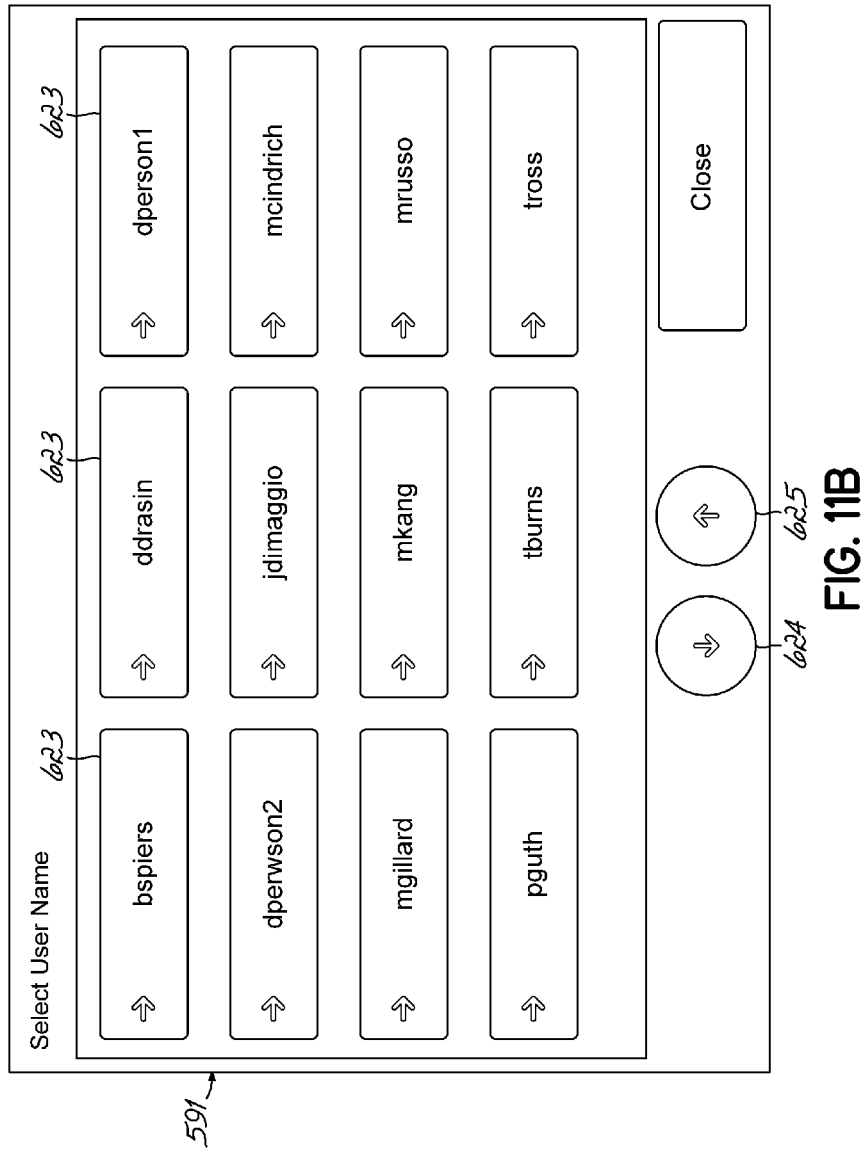

MEDICAL CARE ADMINISTRATION SYSTEM AND METHOD

RELATED APPLICATION

The present application claims the filing benefit of U.S. Provisional Application Ser. No. 60/745,314, filed Apr. 21, 2006, the disclosure of which is incorporated herein by reference in its entirety.

TECHNICAL FIELD

This invention relates generally to a system for ordering, calling for an administration of, and creating a record of, medications and treatments given to patients or residents in a medical care facility.

BACKGROUND

Every medical care facility currently has a paper-based manual or semi-automated system for ordering, calling for an administration of, and creating a record of, medications and treatments given to patients or residents. For example, a long term care facility may consist of resident rooms organized in a number of wings. Each wing may have 10-15 resident rooms with 20-30 residents and one nurses' station. The nurses' station is the administrative center for the wing and is the location where care givers perform paperwork, communicate with physicians, a pharmacy and any other entity required for care of residents in the wing. In such an exemplary facility, a physician makes rounds and creates or changes medication and/or treatment orders for the residents. A nurse may call or fax these orders to the pharmacy and also write the order information on the existing paper charts supplied by the pharmacy the previous month. The pharmacy enters all orders into a pharmacy management system. The pharmacy then prepares associated medications for shipment to the facility. The facility receives medication orders from the pharmacy one or more times per day. The nurse checks the delivery contents and signs the packing list and then, places the orders into appropriate cart drawers with other products. As a service to the facility, the pharmacy prints all orders to be performed on the resident on charts for documentation by the care giver. Throughout the month, the facility submits new orders, discontinues or changes existing orders for entry into the pharmacy computer system and documents these orders in writing on the current month's charts.

Near the end of the month, the pharmacy prints all orders on a series of charts for subsequent documentation. Medication orders appear on a Medication Administration Record (MAR), treatment orders appear on a Treatment Administration Order (TAR) and the combination of medications, treatments and other orders appear on a Physician Order Sheet (POS) which is a master record of resident orders. The pharmacy prints the charts for delivery to the facility for the next month's resident charting. When the facility receives the charts, they compare the newly printed charts to the current month's charts to ensure that the pharmacy received all orders and entered all orders accurately. This tedious process of checking and editing as required may take up to 40 hours per month to complete for an average size facility.

A medication pass is a regularly scheduled activity, which occurs during an interval of time, where medications, treatments and other orders are administered or given to a patient or resident. There are usually four scheduled medication passes per day, for example, in the morning, at noon, in the evening and at night. On each scheduled pass, the nurse reviews a MAR on a cart containing all products for a particular resident to determine which activities or events need to be performed or given during the medication pass. Each order may also contain accompanying vital signs orders alerting the nurse that a vital sign must be taken along with the medication administration. The nurse then prepares the medications, enters the resident room, gives the medications to the resident, and then initials and writes the date and pass time on the MAR. If the resident did not take the medication for some reason, the nurse notes the reason on the chart. If a resident requires an "as needed" medication, the nurse administers it and follow the same charting procedure as the scheduled medication. A treatment pass is similar to a medication pass. At certain times during a day, a nurse may administer treatments, for example, bandage changes, applying ointments, etc. The nurse also initials and charts treatments on a TAR that is a separate record from the MAR in the patient's chart.

The above systems are helpful in preventing errors in the administration of medications and treatments, but are dependent on human paper record keeping activities that, by nature, are not error free. Thus, on occasion, errors do occur in the ordering, dispensing and administration of medications and treatments; and errors further occur in the creation of records associated with those processes.

While automating the above systems may seem simply a matter of following the instructions on an order, such systems are very complex and difficult to automate. For example, when an order is created, it is assigned a rate of reoccurrence based either on the number of administrations within a time period, for example, take three times a day, or at a periodic rate, for example, take every 8 hours. Also, the order will have some prescribed duration, for example, a day, 10 days, 90 days, etc. An automated system may predict or pre-calculate medication or treatment administration schedules over some standard window, for example, 30 days or 100 administrations. The pre-calculated values are stored or printed and serve as a "gold standard" for when the medication or treatment should be administered. In other known systems, the precalculation of a future administration may be made in response to charting an administration of a medication immediately preceding the future administration.

However, the calculation of when a medication or treatment is to be administered is based on many factors; and further many of these factors are likely to change over time. For example, a patient or resident may be moved from one wing of a facility that administers a morning medication at 8 AM to another wing that administers the medication at an earlier or later time. Further, those times may change on a daily basis depending on availability of staff and other factors. When those times change, the pre-calculations of administrations are no longer accurate; and they will either remain inaccurate or will need to be recalculated, for example, mentally by the care giver, who is familiar with the changes.

Under other circumstances, some of the factors required for a pre-calculation cannot be known when the order is created. For example, an order for a pain assessment after an order for "pain medication, as needed" is only required if the pain medication was, in fact, given. Thus, any pre-calculation of administrations of medications and treatments will often be erroneous by the time a medication or treatment is due to be administered.

Further, a pre-calculation of administration of medications and treatments may be based on an iterative series of calculations. In other words, in order to calculate a current administration accurately, an immediately preceding administration has to be calculated accurately. Thus, as the calculations move further along in the series over the administration duration, all intervening administrations must be calculated first and calculated accurately. Further, the rules for calculating a generally iterative series may be complex and therefore, cannot be run on an "as needed" basis using the current information. Thus, there is a tension between the need to recalculate often to increase the accuracy of the predicted administration schedules while at the same time not calculating so often that the system becomes bogged down. The end result is that such a system only meets the goals of accuracy, flexibility, and performance in a limited and compromised fashion.

Thus, there is a need for a system that does not have the disadvantages and faults of the known systems described above.

SUMMARY

The medical care administration system described and claimed herein provides the benefits of an electronic administration record of any type while maintaining known processes of originating medical care orders in a medical care facility and passing the medical care orders to a pharmacy. Therefore, there are no new procedures for nurses to learn in entering written medical care orders into the system. Further, after being transformed into an electronic format, the medical care orders are queued in a computer in the medical care facility, and a nurse simply compares a screen display of the medical care order with the original written order. This process is very efficient and requires only minimal time by the nurse. The nurse has the ability of accept, reject or change the medical care order in the computer before accepting it. While the medical care administration system does not require a nurse to create and electronic entry of the written order, the system does permit a nurse to optionally create an electronic entry of an order if such is deemed necessary, for example, if the pharmacy is closed or if there is an emergency situation.

In one embodiment of the invention, an apparatus provides data that may be used to generate an electronic administration record of a medical care order that was created in a medical care facility. The apparatus includes a facsimile transmission apparatus for transmitting a facsimile copy of a written order for medical care from the medical care facility to a pharmacy. A pharmacy computer stores an electronic pharmacy order for the medical care order; and an application receives the electronic pharmacy order from the pharmacy computer. The application server is operable transform the electronic pharmacy order into first data that is stored in a relational database. The application server is operable to send the first data to a nurses' computer in the medical care facility. The nurses' computer presents on a display screen a first display permitting a comparison between the first data and the written order for medical care, and a second display permitting an acceptance of the first data as accurately representing the written order for medical care.

In a further embodiment of the invention, a method provides data that may be used to generate an electronic administration record of a medical care order created in a medical care facility. The method includes producing a written order for medical care within the medical care facility, faxing the written order for medical care to a pharmacy, converting the written order for medical care to an electronic pharmacy order for medical care, receiving an electronic pharmacy order for medical care with an application server, storing in a relational database first data that may be used to generate an electronic administration record of the medical care order, transmitting the first data to a computer in the medical care facility, comparing the first data with the written order for medical care, and accepting the first data as accurately representing the written order for medical care.

The medical care administration system further utilizes a services oriented architecture to provide an interface with a pharmacy. The architecture provides message formats for different types of medical care orders and respective data definitions in a web services descriptive language. The pharmacy enters the a written medical care order in a pharmacy computer system in accordance with the message formats and data definitions. When the pharmacy sends the pharmacy order to an application server associated with the medical care facility, the pharmacy order is transformed into data that is stored in a relational database and may subsequently be used to create an eMAR. By using the message formats and data definitions, the stored data is in a normative format of definitions that are independent of codes and descriptions that a pharmacy may otherwise use. Thus, if all pharmacies use the message formats and data definitions, the stored data is the same for all substantially identical medical care orders regardless of the pharmacy used. Further, since the pharmacy does the data entry, the burden of that task does not fall on nurses in the medical care facility. In addition, while a pharmacy is converting from a paper MAR system to eMAR system described herein, the paper MAR system may be run in parallel with the eMAR system until the eMAR system is fully tested. Since with the medical care administration system, there is no change in how written orders are sent to the pharmacy, this system testing period of running dual systems places a minimal burden on the medical care facility.

In another embodiment of the invention, an apparatus provides data that may be used to generate an electronic medical administration record of a medical care order created in a medical care facility. The apparatus includes a facsimile transmission apparatus that transmits a facsimile copy of a written order for medical care from the medical care facility to a pharmacy. A website that is accessible by the pharmacy stores a message format for a medical care order and data definitions for the medical care order using a web services description language. A pharmacy computer is operable to store an electronic pharmacy order for the medical care order utilizing the message format and the data definitions. An application server receives the electronic pharmacy order from the pharmacy computer and is operable to store first data in a relational database representing the electronic pharmacy order, the first data being consistent with the message format and the data definitions.

In yet another embodiment of the invention, a method provides data that may be used to generate an electronic administration record of a medical care order created in a medical care facility. The method includes providing a message format for a medical care order and associated data definitions using a web services description language, creating with a computer associated with a pharmacy an electronic pharmacy order for the medical care order using the message format and the associated data definitions, receiving the electronic pharmacy order for the medical care order with an application server, storing in a relational database first data that may be used to generate an associated electronic administration record in a normative format of definitions derived from the message format and the associated data definitions.

The medical care administration system advantageously continuously provides a care giver with up-to-date and accurate information with respect to which medications and treatments are due to be administered. Thus, the medical care administration system eliminates potential disadvantages that arise from precalculated administration schedules due to changes that were made after the precalculated administration schedules were made. Further the medical care administration system automatically creates and maintains accurate electronic MARs and TARs; and further, substantially eliminates all paper associated with the maintenance of records recording administration of medications and treatments.

In a still further embodiment, the invention provides method for operating a system for facilitating an administration of medical care. The method includes storing in a database data for an order for medical care from which can be determined an identity of a person to receive the medical care, an identity of one of a pharmaceutical and a treatment, an order start date, a frequency of administration, an order duration and a time of administration, determining, in response to storing the data for the order for medical care, start and stop times of a first administration interval with respect to the order start date, calculating a number of start times of respective administration intervals occurring between the order start date and a first time after storing the data for the order for medical care, calculating a number of stop times of respective administration intervals occurring between the order start date and the first time, comparing the number of start times to the number of stop times, and determining that the order for medical care is due for administration at the first time in response to the number of start times not being substantially equal to the number of stop times.

The medical care administration system has a computer associated with a cart used to administer the medical care order. The computer advantageously may be operated exclusively by a touch screen and has a series of screen displays that lead a nurse through an administration of the medical care order. The screen displays automatically assist a nurse in performing charting activities associated with a medical care administration, for example, the charting of blood sugar, units of insulin administered and the administration site, when an insulin injection is administered. The screen displays are designed, so the a nurse can electronically chart medical care administrations with little or no training.

In yet a further embodiment of the invention, a method provides data that may be used to generate electronic medical administration records of respective medical care orders created in a medical care facility. The method includes providing first data relating to medical care orders to a computer associated with an administration cart used in administering the medical care orders, generating with the computer a first screen display identifying persons in the medical care facility currently requiring administrations of respective medical care orders, generating with the computer and in response to a first person being selected from the first screen display, a second screen display. The second screen includes a display portion identifying the first person, a first display area identifying medical care orders currently due for administration to the first person, a first button display for selecting a first medical care order, a second display area identifying medical care orders selected for administration, the second display area identifying the first medical care order in response to the first button display being selected, and upon the first medical care order being identified in the second display area, the first medical care order ceases to be identified in the first display area, a second button display for selecting the first medical care order as being administered, a third display area identifying medical care orders ready for charting, the third display area identifying the first medical care order in response to the second button display being selected, and upon the first medical care order being identified in the third display area, it ceases to be identified in the second display area, and a third button display for updating electronic medical administration records for respective medical care orders identified in the third display area.

These and other objects and advantages of the present invention will become more readily apparent during the following detailed description taken in conjunction with the drawings herein.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIGS. 3A-3I are tables of exemplary data definitions for objects used with messages relating to a medication order, a nonmedical order, a discontinued order, resident demographics, physician demographics and an administration override.

FIGS. 4A-4i are examples of screens that may be displayed on a nurses' station computer in a process of accepting an order from a pharmacy and using an optional order entry capability.

FIG. 9 is an exemplary embodiment of a program expressed in a structured query language ("SQL") that determines which orders are currently due for administration.

FIG. 10 is an exemplary embodiment of a mathematical description of a calculation that may be used to determine which orders are currently due for administration.

DEFINITIONS

"Medical care facility" means a hospital, nursing home, long term care facility or other facility in which the health of a patient or resident is tended to, or managed by, an agent or employee of the facility by medical care. While, in general, a patient is often associated with a hospital and a resident is often associated with a long term care facility, for purposes of this document, patient and resident are used interchangeably.

"Medical care" means an administration of a medication or pharmaceutical either prescription or nonprescription or a treatment, for example, taking a temperature, blood pressure, blood sugar level or similar activity, changing dressings, monitoring pain, or other patient related activity.

"Nurse" means any person who provides medical care to another; and in this document, nurse and care giver are used interchangeably.

"Electronic administration record" or "EAR" means any type of administration record for medical care that is generated and stored in electronic form and includes without limitation, a medication administration record, a treatment administration record, or any other medical care administration record.

"Server" means a computer which provides some service, for example, file sharing, for other computers or devices, connected to it via a wired or wireless network.

"Wireless Network" means any type of telecommunications network a part of which transmits data from one device to another without using wires or fiber-optic cables.

"Cache" means memory in a computer that is set aside as a specialized buffer storage that is continually updated and used to optimize data transfers between system elements with different characteristics.

"Floor" value for a real number r is the largest integer no greater than r. Thus, the floor value for 0.85 is zero; the floor value for 2.1 is 2; and the floor value for a negative 1.3 is a negative 2.

DETAILED DESCRIPTION

Figure 1:
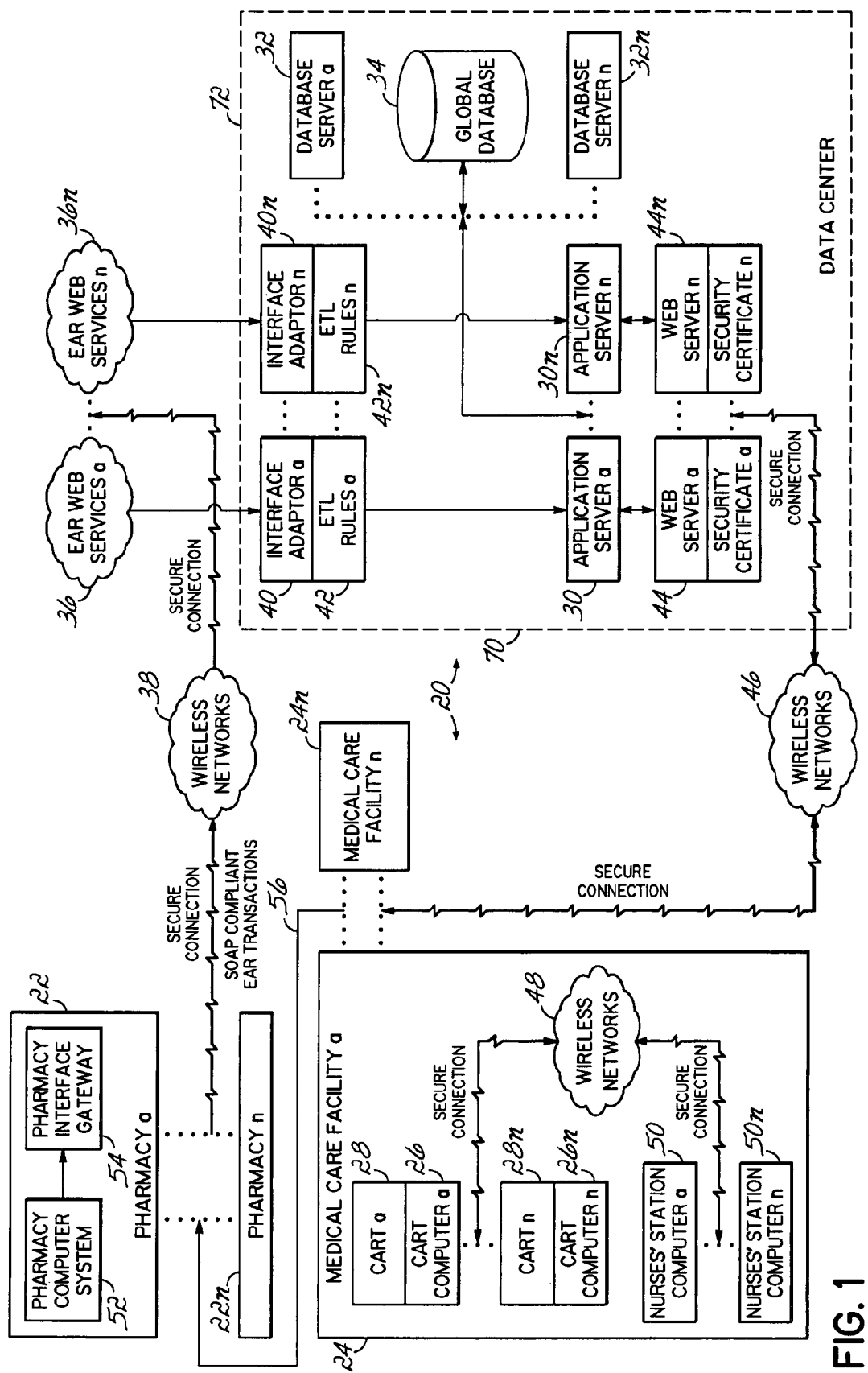
FIG. 1 is a schematic drawing of an exemplary embodiment of a high level architecture or topology of a medical care administration system.

Referring to FIG. 1, in one exemplary embodiment, a medical care administration system 20 is shown interfaced with one or more pharmacies 22-22n and their respective nursing home customers 24-24n. At a high level, the medical care administration system 20 provides an electronic version of a paper-based MAR and TAR commonly used by medical care facilities. The paper-based MARs and TARs are printed by a pharmacy and delivered to a medical care facility once a month and contain instructions to the nurse as to when to give medications and/or treatments and further provide a place to document or chart the administration activity or event.

With the medical care administration system 20, medical care instructions are presented to care givers on screens of respective cart computers 26-26n which are physically located on respective carts 28-28n. The carts 28-28n may be medication carts that contains the medications that are to be administered or treatment carts that contains instruments and supplies used to administer treatments. The care givers also uses the medical care administration system 20 to document, during each medication pass ("med pass"), the fact that medications and treatments were administered along with any other pertinent information that was collected during the med pass. Other pertinent medical care information may include, but is not limited to, blood pressure levels, body temperatures, sites of administrations, other treatments, orders, PRN medications, follow-ups and free-form text notes.

In this exemplary embodiment, the medical care administration system 20 may include one or more application servers 30-30n that are in electronic communications with one or more database servers 32-32n, which in turn, are connected to a relational database 34 that may be implemented with commercially available relational database software from a supplier such as Oracle Corporation. The application servers 30-30n also run respective EAR web services software 36-36n that receives orders for medical care, that is, EAR transactions, from respective pharmacies 22-22n by means of a secure connection over one or more wireless networks 38. The application servers further utilize respective interface adaptors 40-40n with respective transform and load ("ETL") rules software 42-42n to process the orders for medical care and provide corresponding order data to the database servers 32-32n, which control a reading and writing of order data to and from the relational database 34. In addition, the application servers 30-30n are in electronic communications via respective web servers 44-44n, which in turn, have secure connections over one or more external wireless networks 46 and 48 with the cart computers 26-26n and nurses' station computers 50-50n in each of the medical care facilities 24-24n.

The exemplary embodiment of FIG. 1 illustrates that the medical care administration system 20 may utilize multiple components that are generally commonly numbered. However, in other embodiments, only a single one of the multiple components may be used. In the discussion to follow, only one of the multiple components will be referenced. However, it is understood that when the medical care administration system 20 utilizes multiple ones of the various components, its operation is substantially similar to a system utilizing singular components as hereinafter described.

A pharmacy 22 receives a facsimile copy of a written order for medical care via an electronic communications link 56 with a medical care facility 24. The pharmacy 22 often has a pharmacy computer system 52 for day to day operations including medical care order entry and fulfillment. In a process of order entry, the pharmacy computer system 52 utilizes a services oriented architecture provided by EAR web services software 36 running on the application server 30. The EAR web services 36 may provide a website that provides order entry message formats and associated data definitions in a web services description language that provides a Simple Object Access Protocol ("SOAP"). The pharmacy computer system 52 acquires and attaches EAR transaction data relating to an order for medical care, for example, a medication, treatment or other activity. The pharmacy computer system 52 utilizes a pharmacy interface gateway 54 and security certificate 55 to send SOAP compliant EAR transactions over the wireless networks 38 to a website operated by EAR web services 36. The web services 36 accepts data relating to the EAR transactions, that is, a medical care order, sent from the pharmacy computer system 52, checks it for accuracy and then, passes the EAR transaction data through the interface adaptor 40. The ETL rules 42 are applied to the EAR transactions from the pharmacy computer system 52 to provide comparable EAR data using a normative format of definitions that are consistent with the message formats and associated data definitions. The EAR data is transferred by a database server 32 to the relational database 34. The cart computer 26 and nurses' station computer 50 are able to conduct EAR related operations using the EAR data by accessing the relational database 34 via one or more wireless networks 48 in the medical care facility 24 in combination with one or more external wireless networks 46 connectable with the web server 44, the application server 30 and the database server 32.

Each cart 28 has a WINDOWS-based cart computer 26 that runs EAR application software that, as will be subsequently described, guides care givers through a medication and/or treatment administration process in a real-time basis. The cart computer 26 presents respective medication and/or treatment instructions and provides display screens permitting an administration of a medication or treatment, that is, an activity or event, to be documented or charted in the cart computer 26. The cart computer 26 may be any wireless mobile computing device, including laptop, tablet, and handheld computers. The EAR application being run by the cart computer 26 may include a graphical user interface, application business logic, data access logic, and a persistent data cache. The graphical user interface may be developed as a Flash application, which executes in a commercially available Flash player. The business application logic may be written in a general purpose programming language, such as Java technology.

The application server 30 may execute software that provides services to the EAR applications running on the cart computer 26. The application server's services enable EAR applications to search for data, retrieve data, record data, update data, and exchange messages with each other, among others. The application server's services are implemented in business application logic, which may be executed as Java software components running in a Java Application Container that which may be provided by a Sun Microsystems Java Virtual Machine. The application computer 30 also has a cache, and another service of the application server 30 is to synchronize the data in the application server cache with the data in the cache in the cart computer 26. Thus, the cart computer 26 always has current data, so that orders may be accurately and reliably administered.

Each nurses' station has a WINDOWS-based computer 50 that runs a nurses' station application software that gives a nurse a capability of accepting medical care orders that were sent from the pharmacy computer system. In addition, the nurses' station application software provides other capabilities that include, but are not limited to generating reports, adding users to the system, discharging a patient, reading a photo from a digital camera, associating the photo with a patient, entering nurses notes, monitoring late administrations and follow-up activities, placing orders on hold, directly entering orders for medical care, for example, treatments, and indicating if a patient is temporarily out of the nursing home.

One feature of the medical care administration system 20 is to provide the benefits of an EAR, for example, eMAR, eTAR or other electronic administrative record, with minimal impact and minimal change to existing activities and procedures practiced by nurses and other care givers at a medical care facility 26. A further feature of the medical care administration system 20 is to electronically mimic existing activities and procedures used in providing a paper-based MAR or TAR, as well as lead a care giver through a medication pass or other administration activity, so that the system 20 can be used with little or no training.

Figure 2:
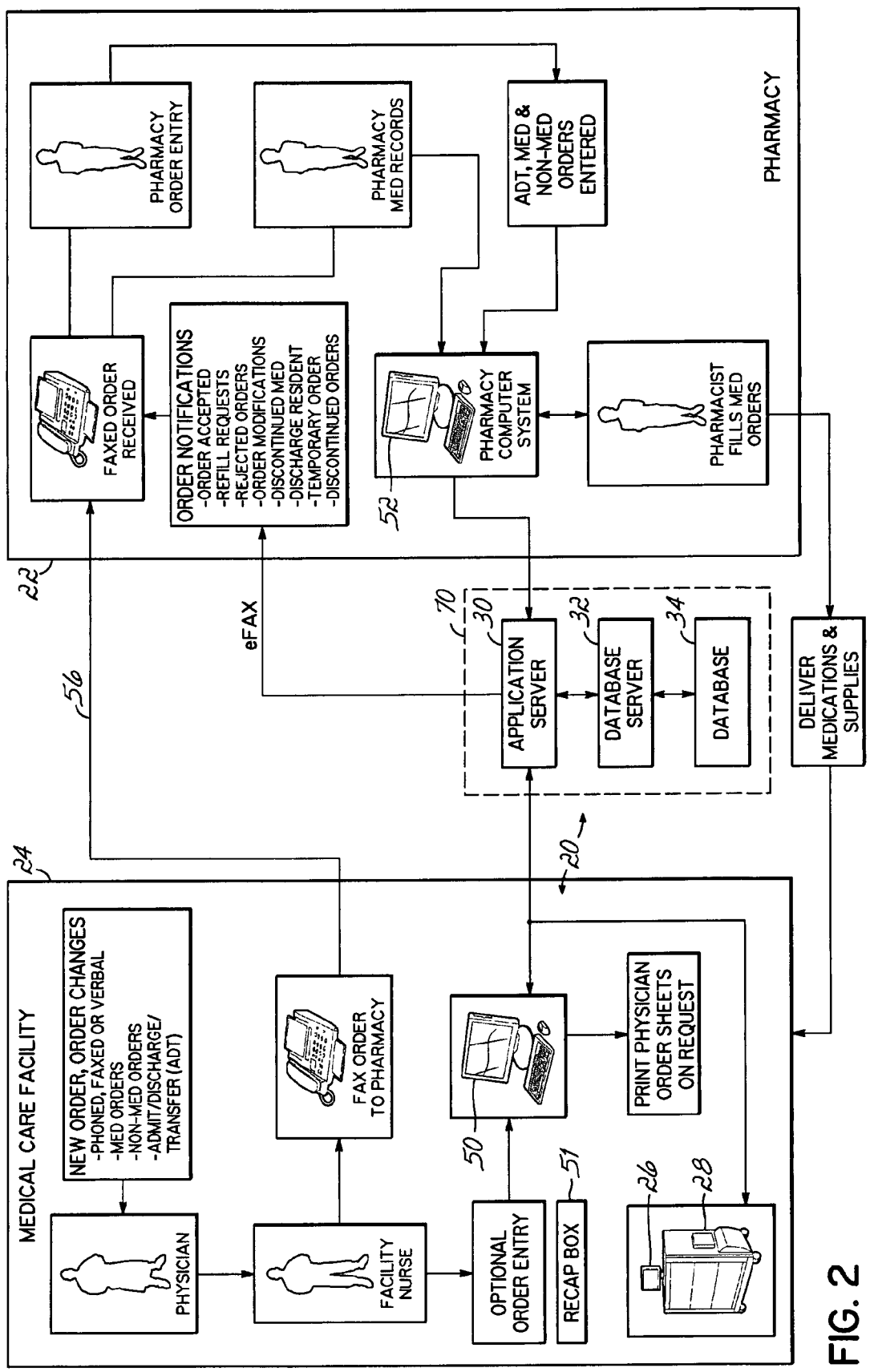
FIG. 2 is a schematic illustration of an exemplary order flow using the medical care administration system of FIG. 1.

The above features are reflected in an exemplary order flow diagram shown in FIG. 2. New orders and changes in orders are communicated by phone, fax or verbally from a physician to a nurse within a medical care facility 24. The orders can be for medications, treatments, PRN medications, follow-ups or relate to an admission, discharge, or transfer ("ADT") of a patient or resident. Most often, a nurse writes the order on a standard form, for example, a telephone order form, and faxes the order to the pharmacy 22 via an electronic communications link 56. The order is also placed in the patient's chart, and a copy of the order is put in a recap box 51 near the nurses' station computer 50. This order entry process is substantially identical to a currently practiced order entry process that is widely used with paper based MAR and TAR systems. Thus, the order entry process is familiar to nurses, is reasonably efficient and does not require any new or unfamiliar data entry activity by the nurse. As will be appreciated, the physician may also fill out an order form from an office and fax the form to both the pharmacy 22 and the medical care facility 24. In any event, with the medical care administration system 20, all written orders for medical care are sent from the medical care facility 24 to the pharmacy 22 by facsimile copy. There is no process in the medical care facility 24 of creating an electronic medical care order comparable to the written order. Nor is there a process in the medical care facility 24 of sending an electronic medical care order to the pharmacy. Further, the substantive information flow relating to medical orders is unidirectional from the medical care facility 24 to the pharmacy 22 via facsimile copy of the written order. There is no electronic communications data link between the medical care facility 24 and the pharmacy 22 providing a bidirectional flow of information relating to the order. While telephonic communications between personnel in the medical care facility 24 and the pharmacy 22 may occur, substantive changes to a medical care order may only be authorized by a facsimile communication from the medical care facility 24 by the pharmacy 22.

Upon being received by the pharmacy 22, the faxed order may be entered into the pharmacy computer system 52 by a pharmacy order entry person. A pharmacist then uses the pharmacy computer system 52 to retrieve, review, approve and print labels for the order. The order is then physically filled either by the pharmacist or by another qualified person. The filled orders whether for medication or supplies are then delivered to the medical care facility 24. The above processes of a pharmacy receiving a faxed order, filling the order and delivering the ordered medications and supplies to the medical care facility are known.

Electronic pharmacy order data relating to the medical care order is then sent from the pharmacy computer system 52 to an application server 30 within the medical care administration system 20. The point in time at which the pharmacy order data is sent to the application server 30 by the pharmacy computer system 52 may vary from pharmacy to pharmacy. In some applications, the data may be sent to the application server 30 immediately after the pharmacy order entry process. In other applications, the pharmacy order data may not be sent to the application server 30 until after the pharmacist has approved the order within the pharmacy computer system 52. In still further applications, pharmacy order data may not be sent to the application server 30 until after the order is filled and ready for delivery. Regardless of the application, the policies, procedures and processes within the pharmacy 22 determine when pharmacy order data is sent from the pharmacy computer system 52 to the application server 30. Further, there is no mechanism by which the application server 30 can override the policies, procedures and practices of the pharmacy with respect to when pharmacy order data is sent to the application server 30. Further still, electronic pharmacy order data flows only unidirectionally from the pharmacy computer system 52 to the application server 30. There is no pharmacy order data flow from the application server to the pharmacy computer system 52.

Referring again to FIG. 1, EAR web services 36 is part of a services oriented architecture and is executed by the application server 30 upon receiving pharmacy order data sent from the pharmacy computer system 52. The pharmacy order data is checked it for accuracy and stored as EAR data in database 34 via the database server 32. The pharmacy order data is generated with the EAR web services 36 using a simple object access protocol ("SOAP") having an extensible markup SOAP/XML format that is consistent with message formats and data definitions as described above. As noted earlier, while there are many commonly used codes and descriptions by different pharmacies, there is no universally accepted format that all pharmacies use to specify the orders received. There are known systems that provide a proprietary interface for each pharmacy, which interprets the codes and descriptions unique to that pharmacy, for example, a HL-7 interface. Such interfaces are costly to develop, implement and maintain. In contrast, with the services oriented technology, each pharmacy may express its order information in a common, relatively user friendly SOAP/XML format. Thus, order data from different pharmacies is provided to the application server 30 in a common structure, organization and format. Further, the pharmacy order data may then be stored in the relational database 34 as EAR data using the normative format of definitions that provides uniform expressions for all of the medical care orders and their respective administrations independent of the pharmacy submitting the order.

The services oriented technology may be implemented in different ways. For example, a single web service message may be defined; and all medical care orders would be expressed by a pharmacy with in the one format of the single web service message. However, in this exemplary embodiment, six different web services messages have been created to handle the various order requirements, for example, a new medication order message, a new nonmedication or treatment order message, a change medication order message, a change nonmedication order message, a refill order message and a discontinue order message. Such different messages are chosen to make the web service messages more user friendly with unique and easily understood functional descriptors and data definitions.

Various rules of use are also provided with respect to each order message. The rules specify what type of orders are to be used with each order message and the data definitions that are associated with each order message. In addition, the web services oriented technology provides numerous SOAP objects defined in the web services description language that may be ASCII text. The pharmacy computer system 52 may support JAVA or C# program stubs that can be compiled to read the SOAP files in the pharmacy computer system 52 and transfer the SOAP files to the application server 30.

Examples of SOAP data definitions for different order objects in the six different order messages are set forth in FIGS. 3A-3I. It is the responsibility of the pharmacy to enter the order into the pharmacy computer system 52 utilizing the SOAP data definitions associated with the particular web services message being utilized. FIGS. 3A-3C present a table of exemplary data definitions associated with a medication order object. FIGS. 3D-3E present a table of exemplary data definitions associated with a nonmedication order object. FIG. 3F presents a table of exemplary data definitions associated with a discontinue and void order object. FIG. 3G presents a table of exemplary data definitions associated with a resident demographics object. FIG. 3H presents a table of exemplary data definitions associated with a physician demographics order object, and FIG. 3I presents an exemplary data definition associated with an administration event override object. While the data definitions of FIGS. 3A-3I present a fundamental group of data definitions for each of the order messages, other data definitions may be created on how to handle different situations that may arise with any particular order message. With each of the pharmacies utilizing a common SOAP/XML format, a respective interface adapter 40 and ETL rules 42 executed by the application server 30 permits a simple mapping of each pharmacy order data being received into normalized definitions of EAR data for a respective medical care order, which is then stored in the relational database 34.

Figure 4A:
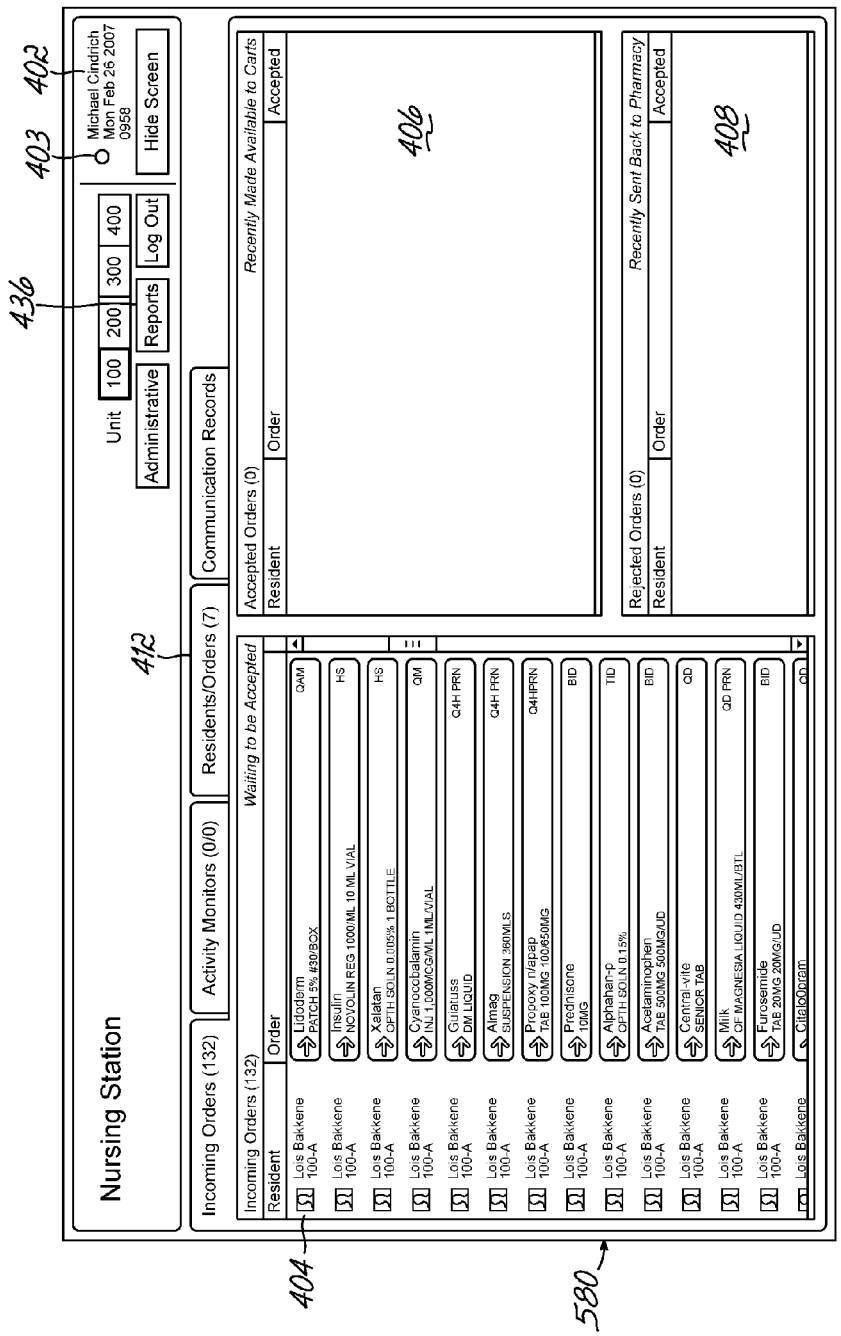

Continuing with a description of the exemplary order flow shown in FIG. 2, upon an order being sent from the pharmacy computer system 52 to the application server 30, the order is then forwarded and queued within a nurses' station computer 50. After a nurse logs into the nurses' station computer 50, as shown in FIG. 4A, an incoming orders display may be provided on a display screen 580. The screen has a first area 402 in the upper right hand corner that displays the current time, date and name of the nurse logged onto the computer 50. A green light display 403 is illuminated if the nurses' station is in communications with the wireless networks required to maintain communications with the application server 30. Thus, the light display 403 is not illuminated while there is a loss of connectivity with the wireless networks. The incoming orders and names of the residents associated with the orders are listed in a display area 404 along the left hand side of the screen display 580. Upon being accepted, an order and its associated resident is automatically moved to an accepted orders area 406. If rejected, the display of the order and the associated resident is automatically moved from the incoming order display area 404 to the rejected orders display area 408 of the screen 580.

In the orders acceptance process, a nurse first identifies and selects an order to be reviewed from the incoming orders display area 404. The selection is often done by using cursor moved by a mouse or keys of a keyboard or touching button displays on the screen display 580 of a touch screen used with the nurses' station computer 50. Upon selecting an order to be reviewed for acceptance, for example, a LIPODERM order, the nurses' station computer 50 provides a screen display 581 shown in FIG. 4B. The nurse then retrieves a copy of the original LIPODERM written order from the recap box 51 (FIG. 2) that was prepared in response to the physicians instructions. The nurse first checks that the medication name, it's strength, and directions presented in the orders display area 450 to match the original written order. If not, the nurse selects the reject button 452. Thus, the order acceptance process is a test of quality of the electronic order data in the database 34. Selecting the reject button 452 causes the screen of FIG. 4A to again be displayed with the LIPODERM order in the rejected orders area of 408. In addition, the rejection of the LIPODERM order is sent to the application server 30, which initiates a LIPODERM order rejection electronic fax to the pharmacy 52.

Figure 4B:

If the medication name, it's strength, and directions are correct for the LIPODERM order as displayed in FIG. 4B, the nurse then checks the prescribed administration schedule, the order grouping, order category, and activities associated with the order to determine whether they match the original order. If not, the nurse may use the button displays in the display area 410 to make the appropriate additions and corrections, so that the screen display of FIG. 4B matches the original written order. In addition, the nurse may enter additional activities that are appropriate, as well as, change an administration schedule by selecting a button display 456, which provides other displays permitting administration times to be selected. When the screen display 581 matches the original written LIPODERM order and appropriate adjusts are made, the nurse then selects the accept order button display 458. The screen of FIG. 4A is again displayed, and the order for LIPODERM is moved from the incoming orders display area 404 to the accepted orders display area 406.

Upon the order being accepted by the nurse, as indicated in FIG. 2, the nurses' station computer 50 provides an electronic copy of the accepted order with any changes back to the application server 30 for storage in the database 34. The accepted LIPODERM order stored in the database 34 is then immediately sent to the cart computers 26. The application server 30 also initiates an electronic fax of the accepted LIPODERM order to the pharmacy 22. As indicated by the order notifications box in FIG. 2, upon input instructions from a nurse, the nurses' station computer 50 may, via the application server 30, initiate electronic faxes to the pharmacy 22 that provide additional instructions to, for example, request refills, reject orders, modify orders, discontinue medications or admit, discharge or transfer a resident. Thus all communications from the medical care facility 24 to the pharmacy 22 are by fax or other transmission that provides a facsimile copy of the original written order.

One feature of the medical care administration system 20 is the ability to accurately determine, at any time, which medications and treatments are due to be administered. The following example will relate to a medication order that is communicated to the pharmacy fax communications as earlier described. Such an order generally includes an identity of a person to receive the medication, an identity of a medication, an order start date, a frequency of administration and an order duration. Information relating to the medication order is then input into the pharmacy computer system 52, sent to the application server 30 for storage in the database 34, accepted at the nurses' station computer 50, and then sent to the cart computer 26.

In most medical care environments, a medication or treatment is considered to be administered in a timely manner if it is administered in a two hour administration interval or window of time that extends from one hour before a prescribed administration time until one hour after a prescribed administration time. For example, a medication or treatment that is prescribed to be given at 9 AM is considered timely administered if it is given in a time interval between 8 AM and 10 AM. Failure to administer in that two hour interval is a failure that can adversely effect the quality of care being given to a patient. Further, as indicated earlier, there are circumstances in which a patient may be moved, staffing may change, a different prescription may be ordered, etc., which may result in a change of medication, treatment and/or a prescribed schedule of administration. It is important that the medical care administration system 20 rapidly responds to those changes, so that the cart computer 26 provides accurate and up-to-date information to a nurse with respect to what medications and treatments, that is, activities or events, are due to be administered.

In contrast to known systems that precalculate times for administration of medications and treatments, the medical care administration system 20 continuously and repeatedly calculates on-the-fly and in real time which medications and treatments are currently due or late at the time of the calculation. Thus, any time a nurse logs onto a cart computer 26, the cart computer accurately displays all medications and treatments that are currently due and provides all the information necessary to administer the medication or treatment. In addition, the administration of the medication and treatment may be electronically charted, thereby permitting administration records, such as MARs and TARs, to be automatically created.

The calculation of administrations currently due may, at different times, be performed for different purposes by either the application server 30, the cart computer 26, the nurses' station computer 50 or another computer within the system 20. Assume for purposes of this example that the medical care order is for a prescription medication and that the calculation is being conducted by the cart computer 26. To facilitate the calculation, the data in the relational database is stored in the cart computer 26 in a number of tables as represented by the entity relationship diagram of FIG. 5, which is an exemplary embodiment of core elements of a data model for calculating which orders for medical care are currently due. The lines and symbols joining the tables represent the cardinality of the data between various tables. Certain data within the tables are assigned global universal identifications ("GUID").

A frequency definition table contains code data that is used to denote a frequency of administration of medical care. For example, the code QD often means a frequency of administration of once per day. A code BID often represents a frequency of administration of twice per day. A code for Q8H often represents a frequency of administration of every eight hours. The codes are contained within the eMAR transactions or orders for medical care that are received from the pharmacy 22. While many of the codes have a universal meaning, there are many other codes that are unique to different pharmacies. The interface adaptor 40 (FIG. 1) and ETL rules 42 provide a mapping layer for a particular pharmacy that transforms the diverse codes in the eMAR transactions from that pharmacy into normative definitions in the form of frequency id's that have a common meaning throughout the medical care administration system 20. For example, if different pharmacies use different codes that, in effect, represent substantially identical frequencies of administration. A common frequency id will be stored in the frequency definition table for those different codes for use by the medical care administration system 20. As indicated by the cardinality symbols the frequency id for a particular order is also placed in an orders table and a frequency definition elements table.

The orders table further contains a resident id that comes from a person table and is created from data representing the first name and last name of the person receiving the medical care. The orders table establishes an order id based on the resident id and a prescription or RX number received from the pharmacy. The orders table further contains a start date for the prescription.

In addition to a frequency id for a particular order, the frequency definition elements table contains a start time and a stop time. The start and stop times define an interval or window of time within which the first administration is due; and as previously discussed, the interval start and stop times are often one hour before and one hour after, respectively, a prescribed administration time. Further, the interval start and stop times are measured in minutes from midnight or 12:00 AM. Therefore, if a first administration is scheduled for 9:00 AM, an interval start time value is 480 minutes or 8 AM; and an interval stop time value is 600 minutes or 10 AM. The frequency definition elements table further contains data relating to a repeat interval in hours or months. Therefore, for a medication that is to be given once per day the repeat hours would have a value of 24. Given the frequency id, start and stop times and repeat interval, the frequency definition elements table establishes a frequency definition element id which is provided to a frequency elements table.

The frequency elements table further contains an order id value and start offset and stop offset values. The start and stop offset values are utilized if the time of the first administration is to be delayed for some period of time after the order start date provided in the orders table. For example, an order from the pharmacy may have a start date of Jan. 1, 2007 but there are instructions not to give the first administration until Jan. 2, 2007. The start offset and stop offset values are stored in minutes. Dimensionally defining the interval start and stop times and the start and stop offset times in minutes provides a system resolution or level of granularity that is distinctive from many known systems. A unique frequency element id is determined from the order id, frequency definition element id and start and stop offsets.

Figure 6:
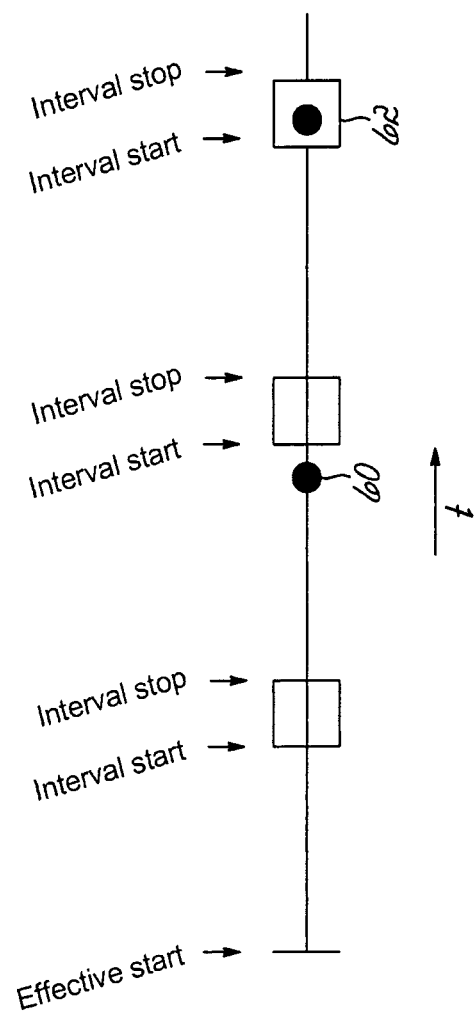
FIG. 6 is a graphical representation of how the calculation determines whether an order is due.

Referring to FIG. 6, an example of a time line of administration interval start and stop times is illustrated. The calculation to determine which orders for medical care administration are currently due simply determines whether the current time is inside or outside of an administration interval. It does this by calculating the number of intervals between a current time and an effective start date of the order. The effective start date is the order start date plus any start offset. If the current time is at the circle 60, there has been one interval start time and one interval stop time from the effective start date. The number of interval start and stop times is equal; and therefore, the current time 60 is between administration intervals, and an administration of the order is not due. However, if the current time is at the circle 62, there have been three interval start times but only two interval stop times. The number of interval start times is not equal to the number of interval stop times; and therefore the corresponding order is due for administration at the current time 62.

Figure 5:
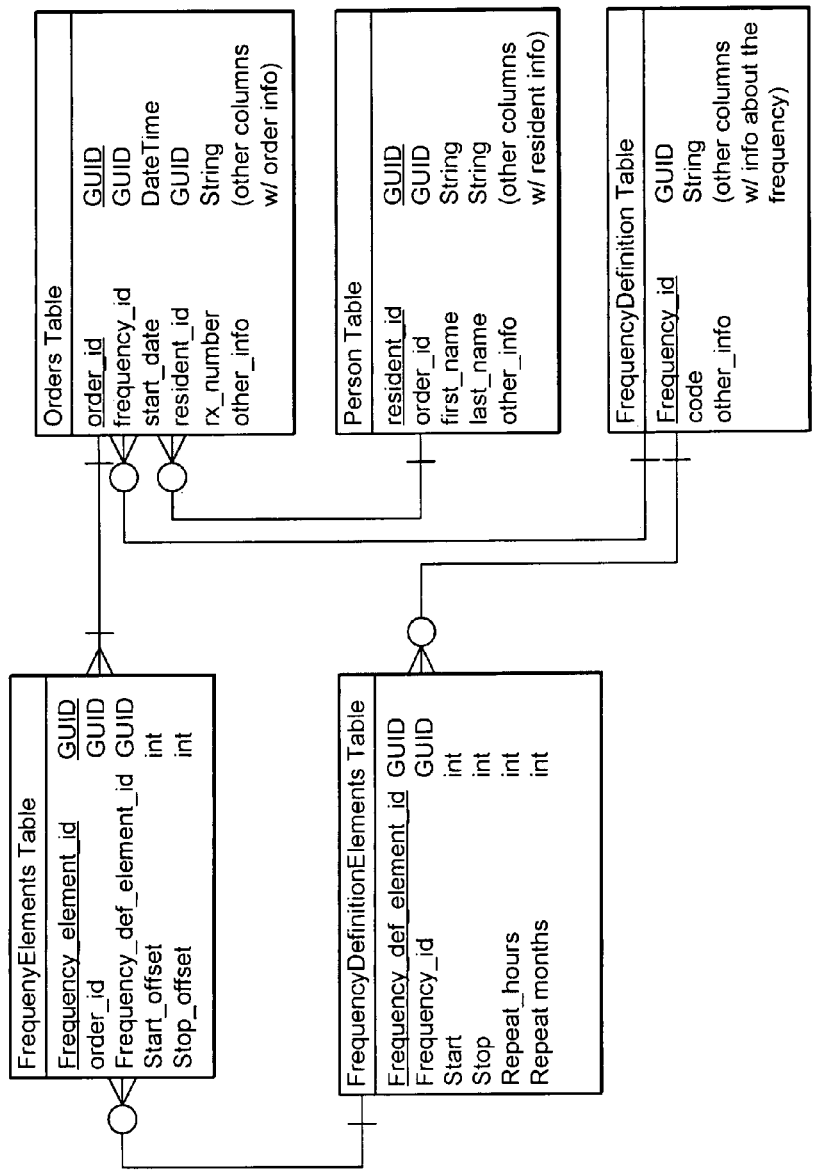
FIG. 5 is an entity relationship diagram illustrating an exemplary embodiment of core elements of a data model for calculating which orders for medical care are currently due.
Figure 7:
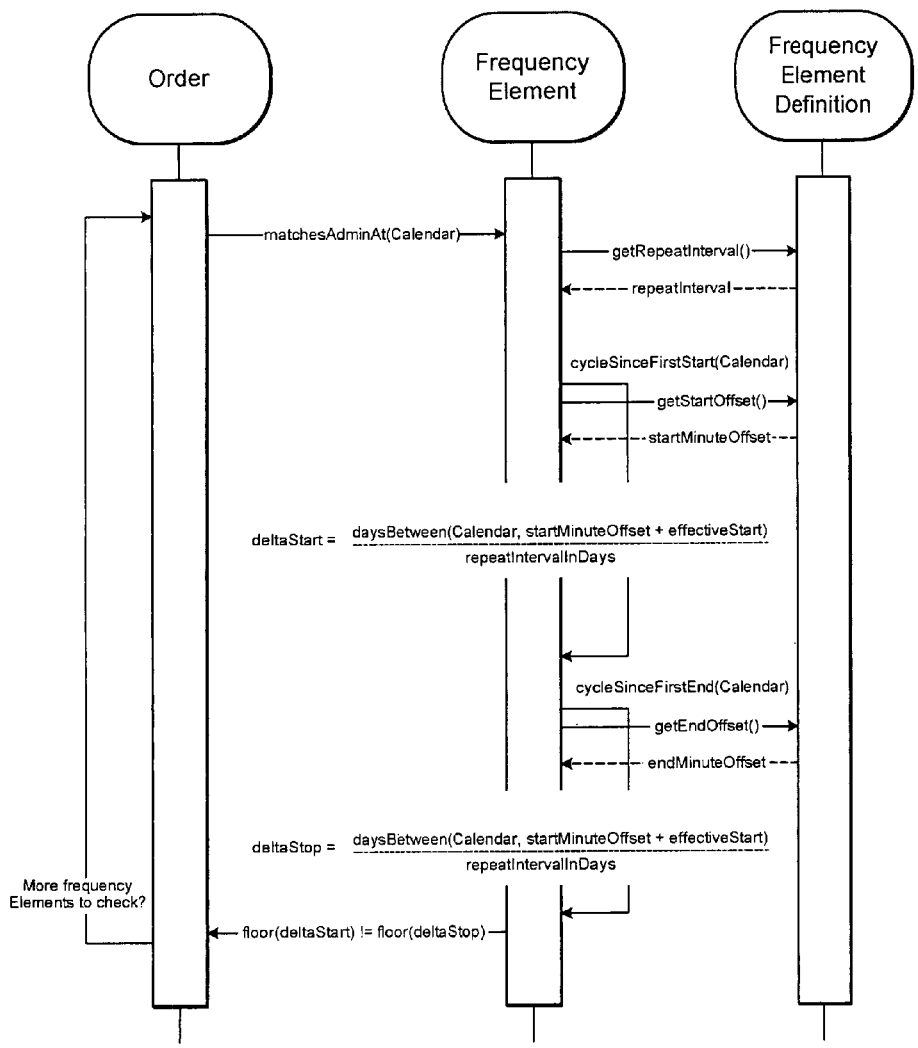
FIG. 7 is an exemplary embodiment of a call graph illustrating how data in the data model of FIG. 5 are used to calculate which orders for medical care are currently due.
Figure 8A:
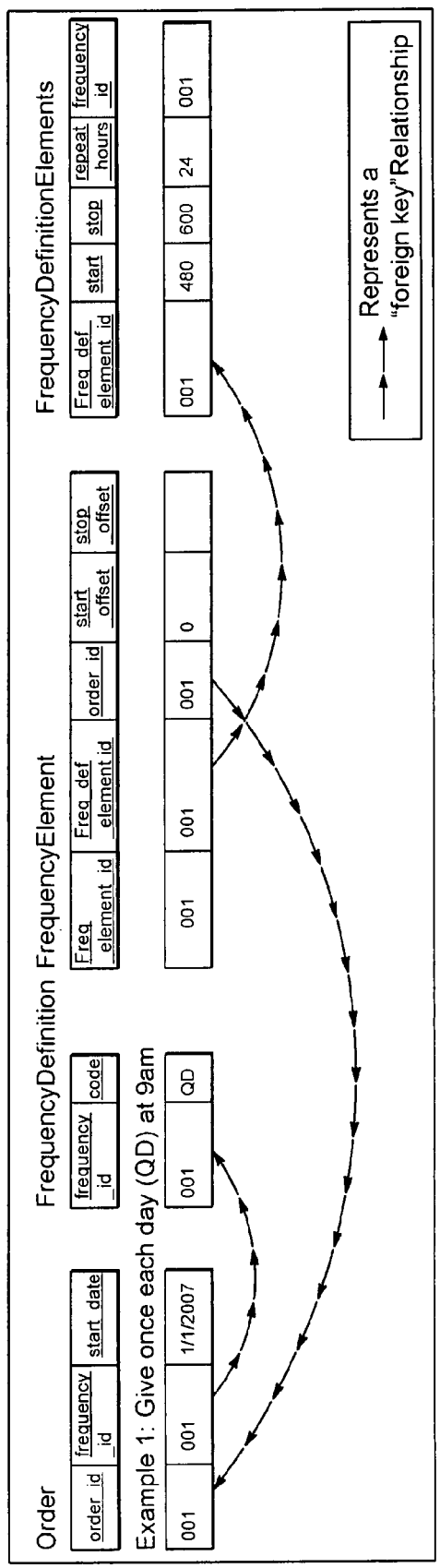
FIGS. 8A-8D are four examples of data and object relationships using the data model of FIG. 5 for four different frequency of administration schedules.

The calculation to determine whether an administration for a medication is due is further expressed in a call graph of FIG. 7, which shows how the calculation utilizes the data in the tables in FIG. 5. Further, FIG. 8A illustrates a specific example of data and object relationships using the data in the tables in FIG. 5 for a calculation of a frequency of administration code QD, that is, an administration once per day. Assume a start date in the orders table of Jan. 1, 2007, a first administration time of 9 AM and further assume that the start and stop offsets are zero. That provides in the frequency definition elements table, an interval start time of 8 AM or 480 minutes and an interval stop time of 10 AM or 600 minutes. The repeat interval of once a day is 24 hours. Further, assume that the current time is 9 AM on Jan. 3, 2007. Referring back to the call graph of FIG. 7, assuming a zero start offset, the first interval start time is 480 minutes after the effective start date of midnight Jan. 1, 2007, that is at 8 AM. The delta start is determined by calculating the number of hours from the first interval start time to the current time of 9 AM on Jan. 3, 2007, that is, 49 hours. That interval is divided by the repeat interval of 24 hours to provide a delta start value of 2.04. A similar calculation is preformed with respect to the interval stop time. The first interval stop time is 10 AM on Jan. 1, 2007 which is 47 hours before the current time of 9 AM on Jan. 3, 2007. That value is divided by the 24 hour interval to yield a delta stop value of 1.96. The mathematical floor values of the delta start and stop values are respectively 2 and 1. Since, at 9 AM on Jan. 3, 2007, the number of interval start times is different from, or not equal to, the number of interval stop times, it is determined that the current time is within an administration interval. Therefore, the medication associated with this order is now currently due for administration to the patient.

Taking another example of a current time of 7 AM on Jan. 3, 2007, the current time is 47 hours from the first interval start time of 8 AM, which when divided by the interval time of 24 hours, provides a delta start value of 1.95. The current time of 7 AM on January 3rd is 43 hours from the first interval stop time, which provides a delta stop value of 1.79. The floor values of the delta start and delta stop values are both 1 and thus, equal. Therefore, the calculation determines that the current time of 7 AM on Jan. 3, 2007 is not within an administration interval for this order.

Figure 8B:
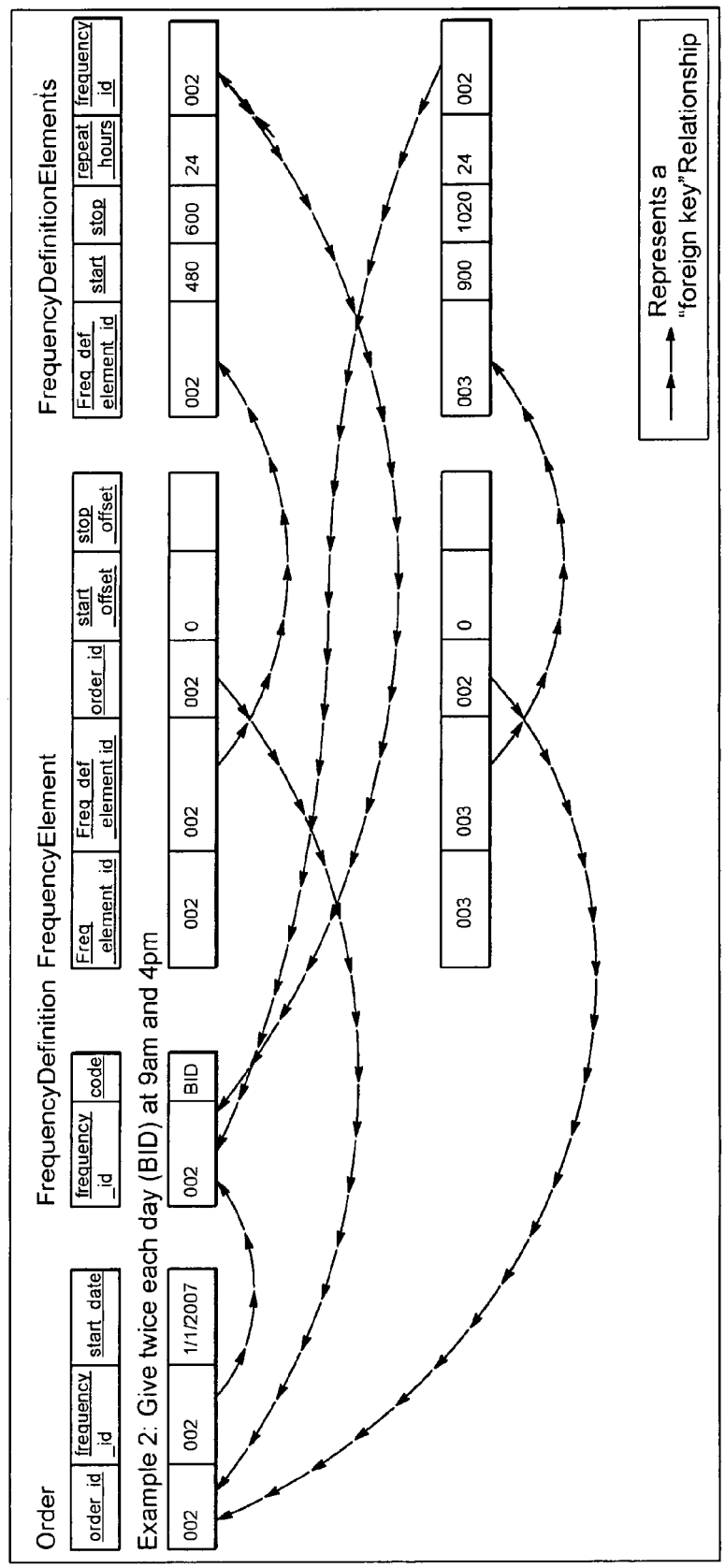

A further example is shown in FIG. 8B in which an administration frequency code of BID means a frequency of administration of twice a day. In this example, the administrations are scheduled for 9 AM and 4 PM each day. Further, in this example, each administration schedule has its own frequency element id; and two separate interval calculations are made for the two respective administration schedules. The first administration schedule has an interval start time of 8 AM or 480 minutes after midnight and an interval stop time of 10 AM or 600 minutes after midnight. The second administration schedule of 4 PM has an interval start time of 3 PM or 900 minutes after midnight and an interval stop time of 5 PM or 1200 minutes after midnight.

Figure 8C:
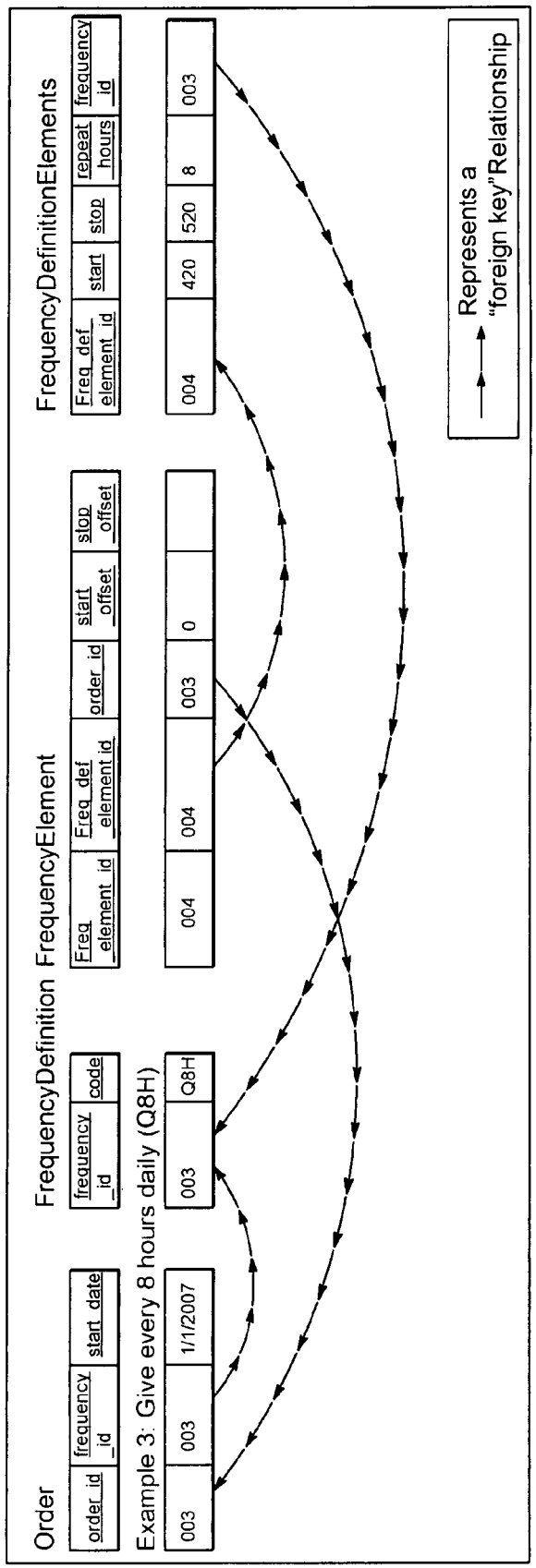

Referring to a further example in FIG. 8C, the frequency of administration code Q8H identifies a frequency of administration of every 8 hours daily. The administrations are equally spaced over a 24 hour period; and thus, the repeat hours interval in the frequency definitions elements table may be set to 8 hours. Further, the interval start time is 7 AM or 420 minutes; and the interval stop time is 9 AM or 540 minutes.

Figure 8D:
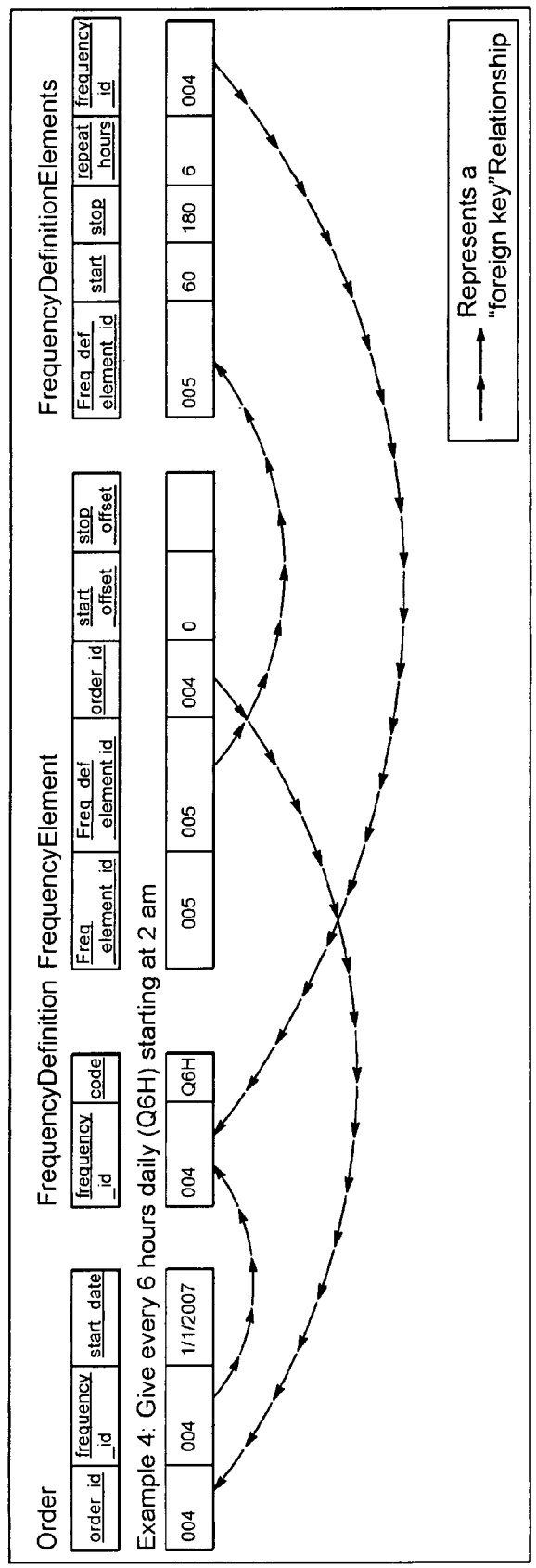

FIG. 8D shows a further example in which a frequency of administration code Q6H means an administration every 6 hours daily starting at 2 AM. In this example, the repeat interval is set to every 6 hours. The interval start time is 1 AM or 60 minutes, and the interval stop time is 3 AM or 180 minutes.

FIG. 9 is an exemplary embodiment of a program expressed in SQL that determines which orders are currently due for administration. In addition, the calculation of which orders are currently due for administration can be expressed as a formal mathematical description as set forth in FIG. 10. The mathematical description assumes that all units are normalized before, during or after operations. This normalization procedure is omitted in this description both for generalization of the description as well as clarity and brevity.

The calculation is repeated executed by the cart computer 26 with sufficient frequency that the identities of administrations due for persons in the medical care facility displayed by the cart computer 26 is always up-to-date. The calculation can be executed every time that the cart computer 26 detects a change in data relating to an order administration schedule. The calculation may also, or alternatively, be periodically executed based over fixed or variable time intervals; and further, the time intervals may vary from seconds to hours depending on a level of activity at any particular time. While the above example of the calculation is directed toward a medication order, the calculation is equally applicable to orders for treatments and other activities requiring charting, including but not limited to blood pressure, pulse rate, blood oxygen level, respiration, weight, pain assessment, intervention, lung sounds, PRN administration, PRN follow up, oral supplements and other activities required for medical care. Thus, presuming orders for medical care, and any changes thereto, are properly entered by a pharmacy into the system 20, the display on the cart computer 26 identifying all administrations of medical care due is a very accurate and reliable representation of the state of medical care required for the residents and can be relied on with a very high level of confidence.

The above-described calculation engine uses an algorithm that is non-iterative and can be executed using a declarative, non-procedural execution language, for example, SQL. Thus, the cost of calculating administrations that are due is constant and does not grow over the duration of the order for medical care. Further, the cost of the calculation is exceedingly small and may be easily amortized over a large data set. The constant and small calculation cost allows a dynamic, on-the-fly, real time determination of when medical care administrations are due at a time when a nurse is ready to administer the order to a patient. Hence, determinations of when medical care administrations are due are made with the up-to-date data at a time when they are needed rather than ahead of time. This allows users of the medical care administration system to change parameters that affect an administration of an order, for example, transferring a patient to another room or wing, rescheduling of a medical care administration, changing a prescribed time for medical care, etc., without worry of effecting the quality of medical care. The dynamic, real time determinations of when medical care administrations are due automatically accommodates all changes in parameters and is superior to other systems that precalculate administration schedules that may become unreliable with subsequent changes in parameters.

At this point, a medical care order originated by a physician or nurse at the medical care facility 24 has been faxed to, and processed by, the pharmacy 22, sent to the application server 30 for storage in the database 34, accepted by a nurse at the medical care facility, identified as an active order in the database 34 and sent to the cart computer 26. The cart computer 26 continuously executes calculations, as described above, for all accepted but unadministered orders in the medical care facility 24 to identify which orders are due for administration. The cart 28 and cart computer 26 are used by a nurse or other care giver to pass medications or treatments. The updating of the EAR during a med pass is highly automated, and one feature of the medical care administration system 20 is to facilitate the med pass while updating the eMAR. In other words, the updating of the EAR should not create extra work for the nurse but instead, should make the med pass easier for the nurse. Therefore, as shown in FIG. 2, the cart computer 26 has a display screen 27, for example, a touch screen, a tablet or comparable screen. The touch screen allows a nurse to enter selections by simply touching the screen. In some applications, an input keyboard and/or a mouse may be provided for use depending on a nurse's comfort level with a particular input device. Further, the display screens are organized to lead a nurse through a medication administration or pass process that is very similar to an existing paper MAR system, with which a nurse is very familiar. The difference is with the medical care administration system 20, there is no paper or paper record to be maintained.

Figure 11A:
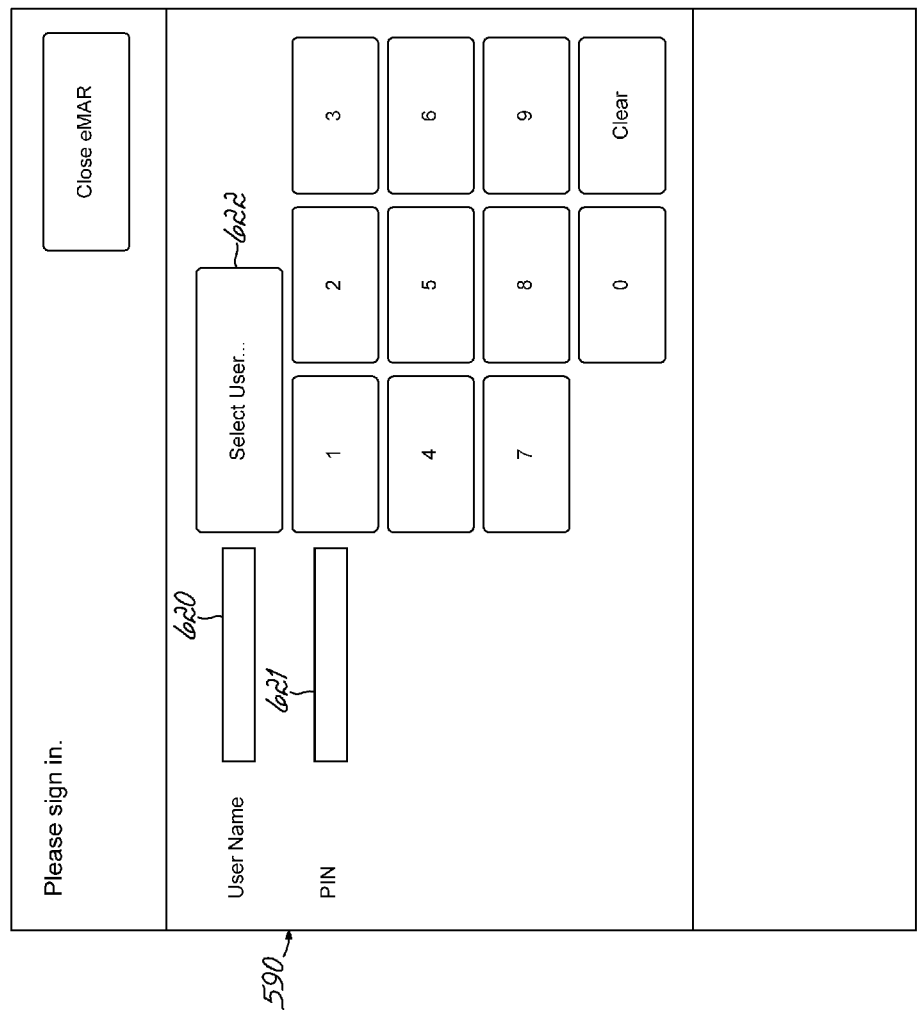
FIGS. 11A-11T are exemplary representations of screen displays that may be used in an administration and electronic charting of a medical order.
Figure 11C:
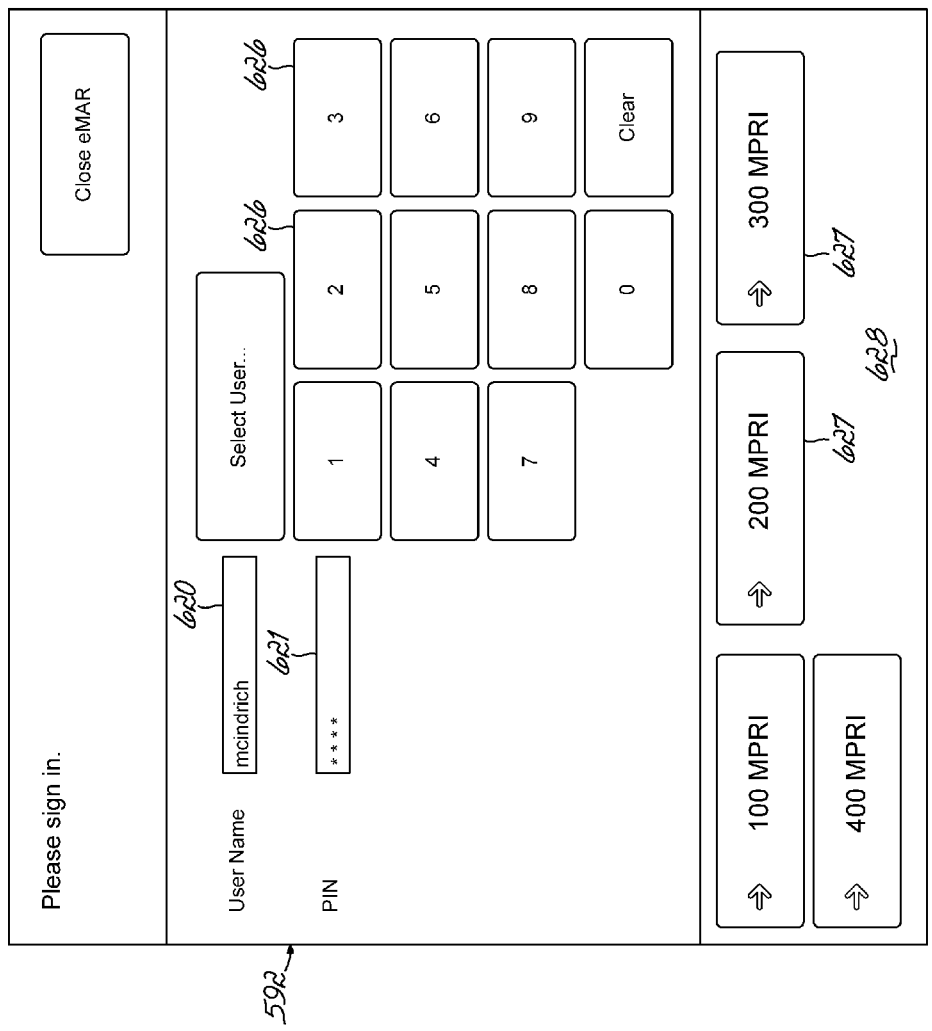
Figure 11D:
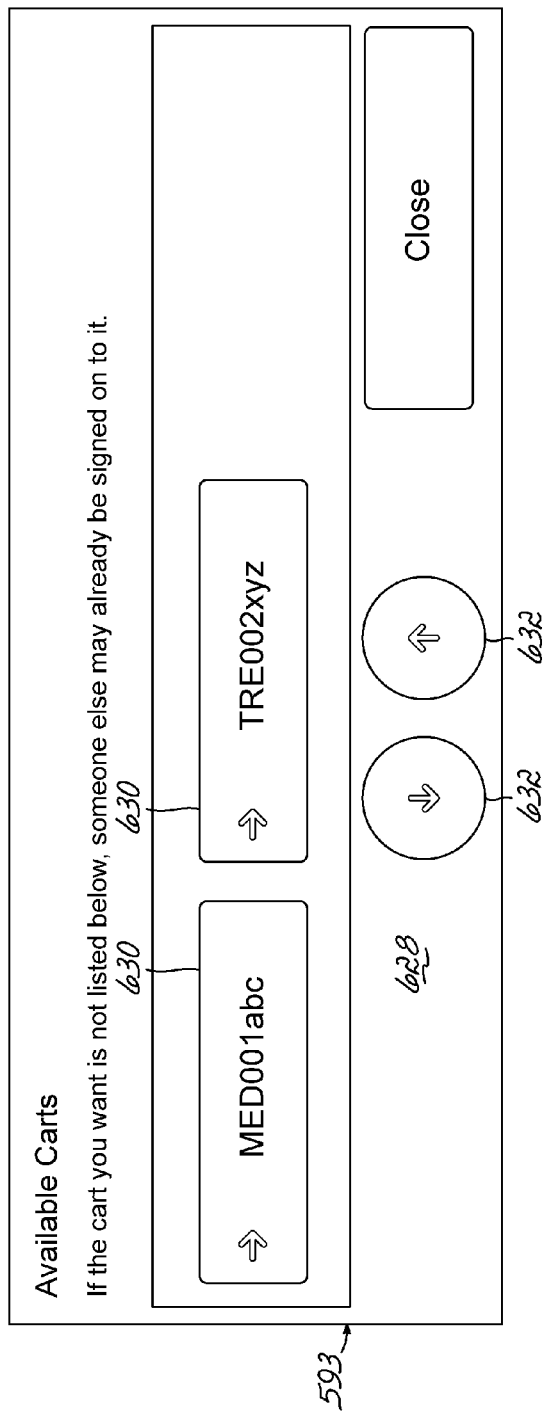

Whether the cart 28 is a medications cart or a treatment cart, the cart computer 26 executes an application program that is utilized to electronically chart administrations of medications, treatments, other orders such as blood pressure and lab work, and follow ups such as the effectiveness as a PRN medication or patch removal. Referring to FIG. 11A, the display screen 27 provides a log in screen display 590 in which the nurse can enter a user name in window area 620 and a pin number in window area 621 utilizing a key board (not shown). Alternatively, the nurse may choose to touch the select user button display 622; and as shown in FIG. 11B, a screen display 591 displays a listing of potential users. The nurse may select a user name by touching one of the display buttons 623 identifying the potential users. Other names can be displayed by touching the up and down cursor key displays 624, 625. Upon touching one of the user button displays 623, a screen display 592, as shown in FIG. 11C, provides number key displays 626 that may be touched to enter a pin number in the area 621. Thereafter, the nurse selects or touches one of the button displays 627, which identify particular unit locations within the medical care facility 24. Upon a unit location being selected, the area of the screen 628 is replaced by a screen display 593 shown in FIG. 11D. The screen area 628 now presents button displays 630 identifying carts 28 available for use. Cursor displays 632 may be touched to scroll through a listing of the available carts. Each cart has a label with its identification, and a particular cart is chosen for use by touching a button display 630 corresponding to that cart's identification label. The log in process is now complete. It should be noted that portions of the above log in process may also be achieved by utilizing a personal identity card that stores data utilizing a magnetic data strip, a radio frequency identification device or other comparable storage medium.

As previously described, the cart computer 26 iteratively executes the administrations due calculations on all of the orders in the medical care facility 24; and therefore, the cart computer 26 can accurately identify, at any time, which orders are currently due for administration. Upon completion of the log in process described above, the cart computer 26 then provides the screen display 594 shown in FIG. 11E, which provides graphical displays of all of the orders currently due for administration. A main screen display area 640 contains a photo identity 642, a name 644, and a room and bed location 646 of all persons for whom orders are currently due. The order in which such persons are displayed may be organized differently for different applications. For example, they may be displayed in room number order, which may be most convenient if a nurse is assigned to a particular unit in the medical care facility. They may also be displayed alphabetically by last name, or they may be displayed with the administrations having the oldest administration start intervals displayed first. In some applications, the display order of objects in the display area 640 may be selectable by the nurse.

A left hand screen display area 648 provides further information as to the number of medications due, the number of treatments due, the number of other administrations due and the number of follow ups in respective screen areas 660, 662, 664, 666. In addition, each type of order has a graphical tag or icon, for example, an M tag for medications due, a T tag for treatments due, an O tag for other administration, and an F tag for follow ups due. Further, those tags are associated with the persons identified in the display area 640 to clarify the type of administration due for each person. The screen display area 648 has a display line 658 and associated tag 668 that identifies those persons to whom medical care is currently being administered by another nurse. There are also persons 669 identified in the display area 640 that have none of the tags 660, 662, 664, 666 associated with them, and therefore, no administrations are currently due for them. However, such persons 669 may be selected for the administration of PRN medications. The screen area 648 also contains a line display 670 in which the number of orders awaiting approval at the nurses' station computer 50 is identified. The screen area 648 further includes a log out button display 672, a quick help button display 674, a hide screen button display 676. Display area 678 provides a current time, date and identity of the nurse currently logged into the cart computer 26. In addition, an indicator light display 680 stays illuminated as long as the cart computer 26 is online with required wireless networks. The light display 680 goes out when the cart computer 26 loses its connection with the application server 30.

Figure 11E:
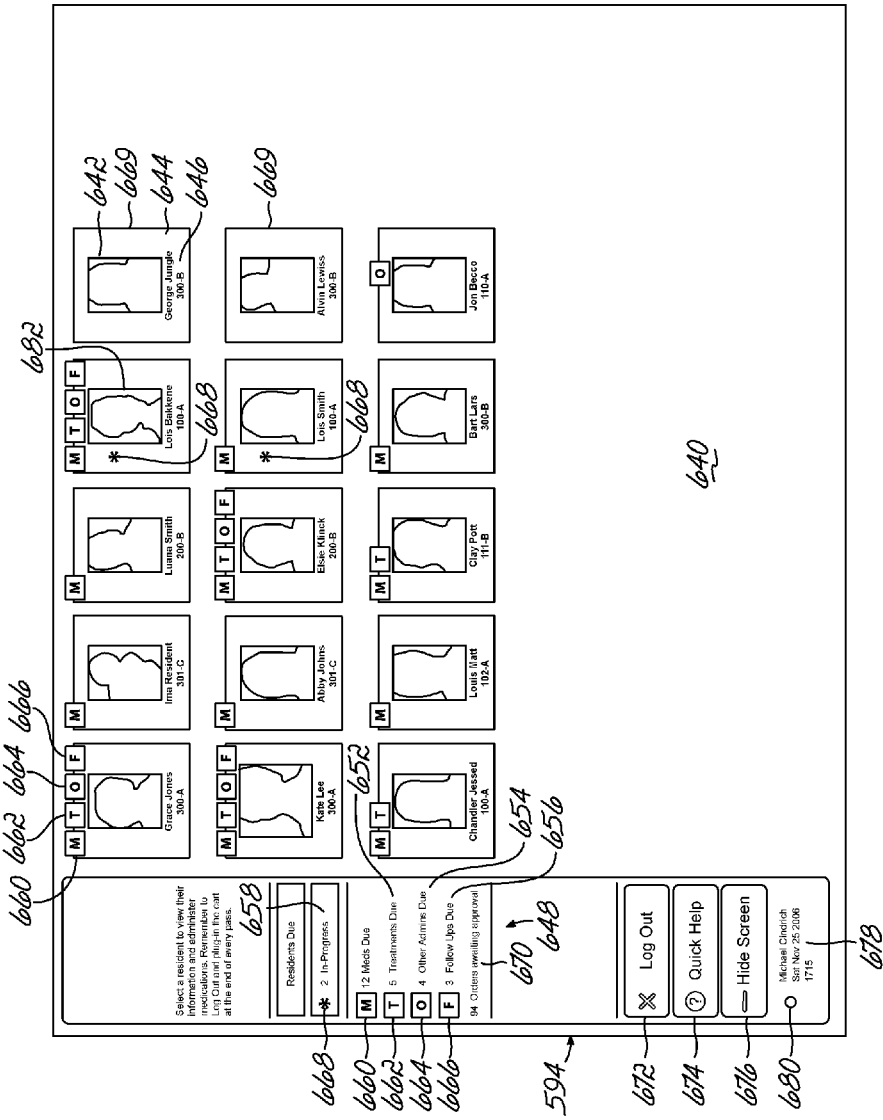
Figure 11F:
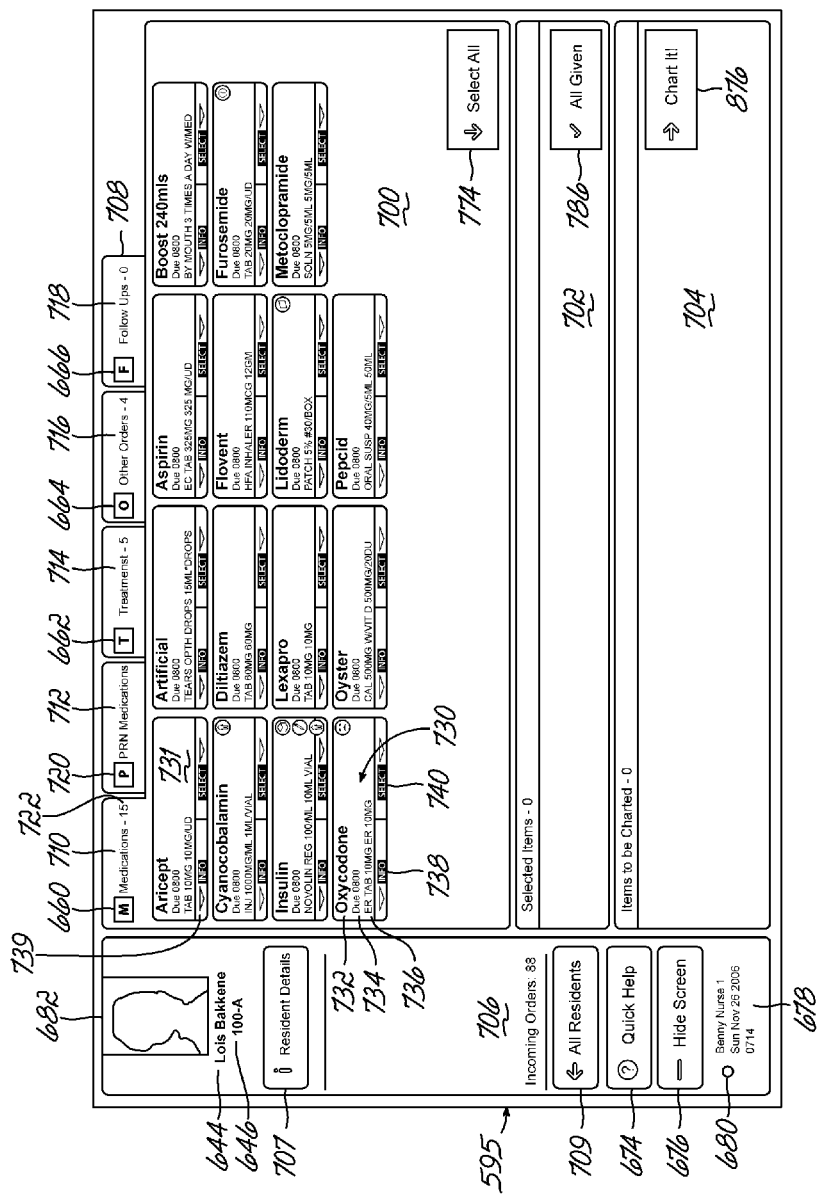

After reviewing the screen display of FIG. 11E, the nurse touches a picture of a particular resident to whom an order is to be administered, for example, the picture 682. Referring to FIG. 11F, a profile screen display 595 for that person is then presented by the cart computer 26. The screen display 595 is divided into an orders due display area 700, an orders selected display area 702, a ready for charting display area 704, a side bar display area 706, and a top bar display area 708. The top bar display area 708 contains tabs identifying the types of administrations due, for example, a medication tab 710, a PRN medication tab 712, a treatment tab 714, an other orders tab 716 and a follow up tab 718. Each of those tabs has a respective tag 660-666, 720 as well as a display of the number of administrations due with each tab, for example, as shown at 722 of the medications tab 710. When it first appears, the resident profile screen display 595 defaults to the medications due tab 710; and all of the medications due for this person are listed in the orders due area display 700. Each medication order due is identified in its own button display 730 that contains an identity of the medication 732, a prescribed administration time 734 and a description of the medication 736.

The side bar display area 706 contains a photo identity 642, the person's name 644, and a room and bed location 646. A resident details button display 707 may be used to obtain demographic information about the person similar to that contained on a face sheet of a paper chart. The side bar display area 706 further has an all residents button display 709 that may be used to return to the screen display 594 of FIG. 11E. Displays 674, 676, 678 and 680 are substantially identical to the similarly numbered displays described with respect to FIG. 11E.

Figure 11G:

Each medication order touch button 730 includes an info button display 738 and a select button display 740. If a nurse is new or unfamiliar with the resident and/or the resident's medical care, any of the info button displays 738 may be touched to get further information about a particular medication to be administered. For example, if an info button display 739 for ARICEPT is touched, a screen display 596, as shown in FIG. 11G, is presented providing further details about the ARICEPT medication order and its prescribed administration. This screen has a top bar display area 742 that identifies the ordered medication and an adjacent display area 744 that identifies the prescription number, the physician and order date, A middle display area 746 displays an administration start date 748, a further description of the ordered medication 750, a prescribed administration time 750 and a prescribed frequency of administration 754. The screen display 596 has another display area 760 containing a history button display 762 for displaying an order administration history, a refill button display 764 for sending an electronic fax to the pharmacy requesting an order refill, and a discontinue button display 766 for sending an electronic fax to the pharmacy requesting that an order be discontinued. The screen display 596 further has a close window button display 770 that when touched returns the user to the screen display 595 shown in FIG. 11F.

Figure 11H:
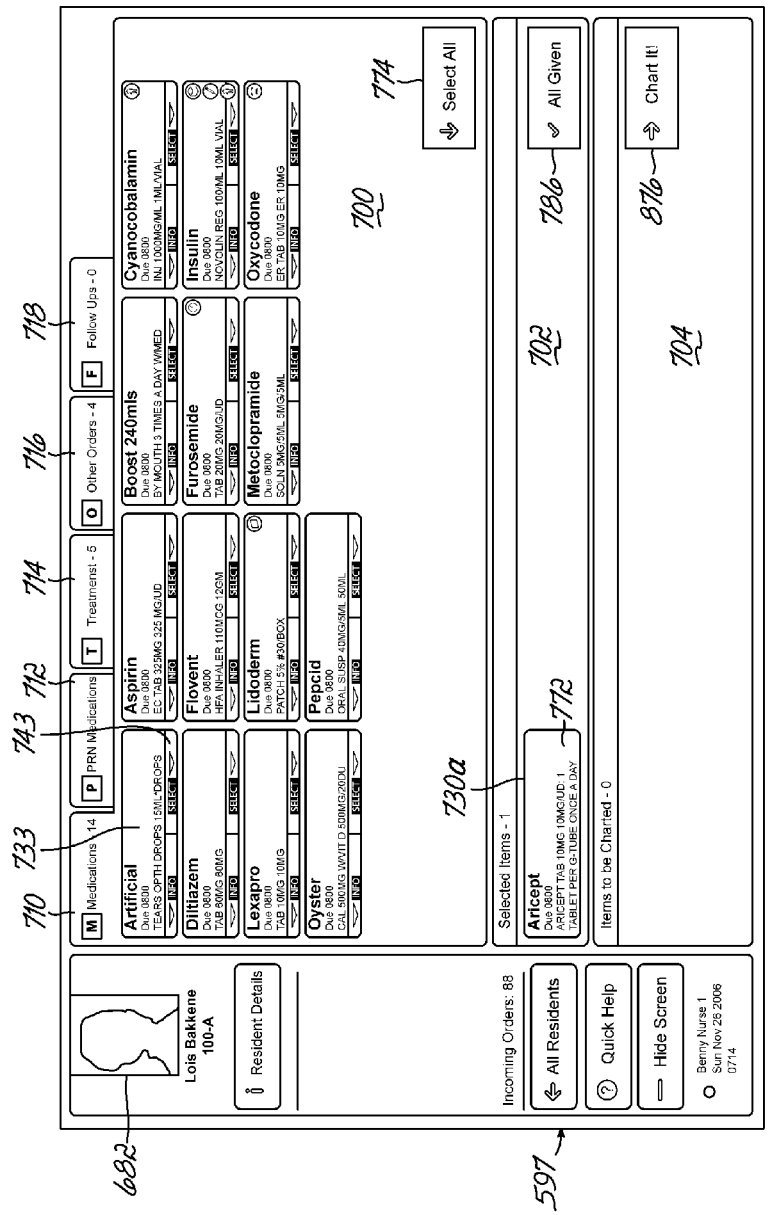

A select button display 768 may be touched to select the ARICEPT medication order identified in FIG. 11G. Upon touching the select touch button 768, as shown in FIG. 11H, a screen display 597 is presented that is similar to the screen display 525 of FIG. 11F, except that in this screen display 597, a button display 730a for ARICEPT now appears in the orders selected display area 702 and has been dropped from the orders due display area 700. In addition, the button display 730a contains additional information 772 further describing ARICEPT and its administration schedule. In an alternative embodiment, a nurse may use a bar code reader to read a bar code on one or more of the medications being administered. The cart computer 26 decodes the read bar codes, selects a corresponding medication from the orders due display area 700 and moves the selected order to the orders selected display area 702.

Figure 11I:
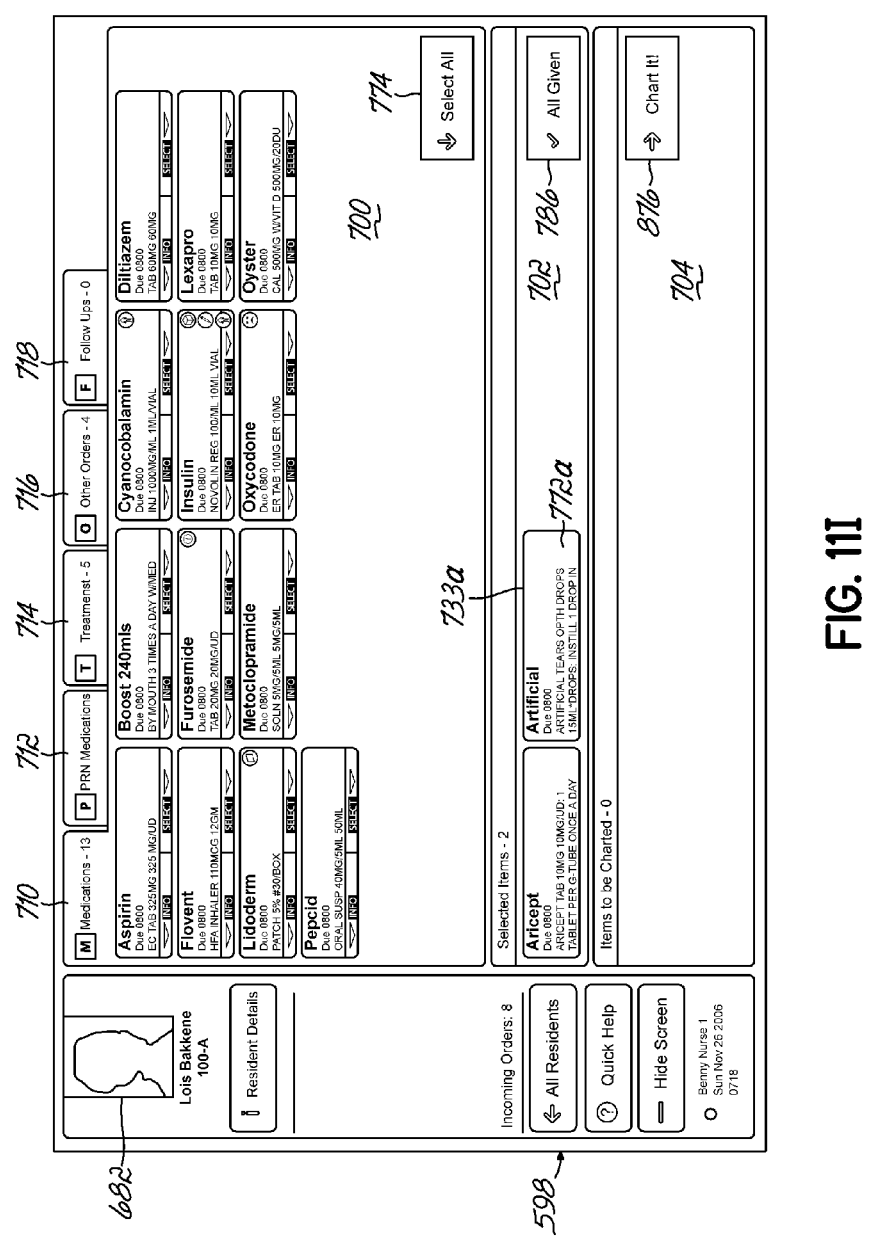

In some situations, a nurse may be familiar with some of the medication orders identified in the orders due screen display area 700 of FIG. 11H. For example, if the nurse is familiar with the administration of ARTIFICIAL for this resident, the nurse may simply touch the select button display 743 within the ARTIFICIAL display button 733; and the screen display 598 of FIG. 11I is presented. Again, the selected ARTIFICIAL medication order has been moved from the orders due display area 700 to the orders selected display area 702; and the button display 733a includes additional information 772a further describing ARTIFICIAL and its administration.

Figure 11J:

Referring back to FIG. 11F, if a nurse if very familiar with the resident's medical care and administrations have not changed. Upon reviewing the orders displayed in the orders due display area 700, the nurse may choose to touch the 0 button display 774, which results in a screen display 599 as shown in FIG. 11J. All of the medication orders that were previously displayed in the orders due display area 700 are now displayed in the orders selected display area 702 with additional information about the medication due and it's administration schedule. In this display, the orders accepted display area 702 has expanded to present all the accepted orders, and the orders due display area 700 has shrunk.

Figure 11K:
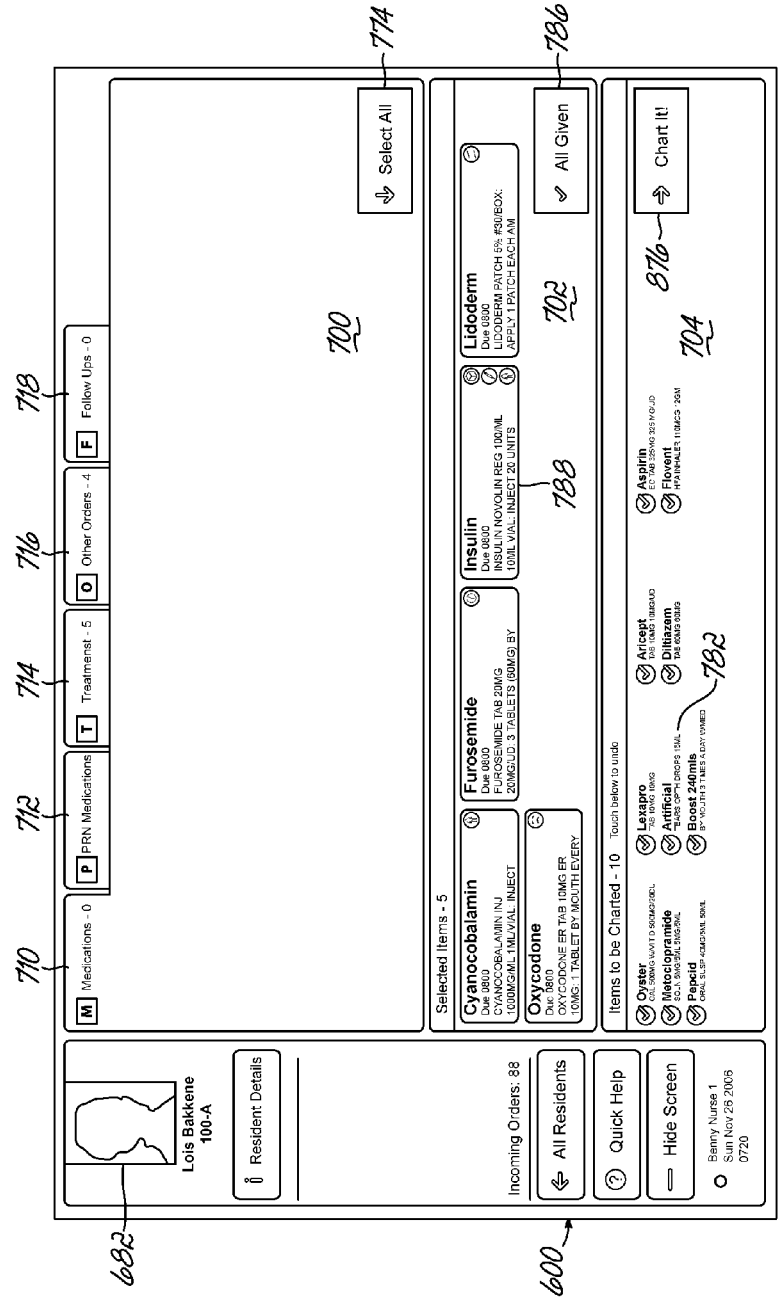

At this point, the nurse may observe that certain administrations require additional activities. For example, the insulin button display 735, has tags 780 along a right hand side of the button display 735. Each of those tags identifies an additional activity that is required with an injection administration of insulin, for example, charting of a blood sugar level, insulin units given and an administration site. However, other button displays, for example, the ARTIFICIAL button display 733, do not have associated tags and can be administered without preforming other activities. Thus, a nurse may choose to administer those medications first. Those medications are removed from the medication cart and administered to the resident. When the administrations are complete, the nurse returns to the medication cart and touches the button displays 733 associated with those administered medications. As shown in the screen display 600 of FIG. 11K, the selected administered medications no longer appear in the orders selected display area 702 but are now displayed in the ready for charting display area 704.

Figure 11L:

The medication button displays remaining in the orders selected display area 702 all require the charting of additional activities. For example, as discussed earlier, upon an administration of insulin, a nurse must chart a blood sugar level, a number of insulin units given and a site of the injection. Further, the insulin button display 788 cannot not be moved from the orders selected display area 702 to the ready for charting display area 704 until charting of the additional activities have been completed. To enter the information relating to the additional activities, the insulin button display 788 is touched; and a screen display 601 is presented as shown in FIG. 11L. The screen display 601 has a first display area 800 that provides information similar to that as shown in the screen display 596 of FIG. 11G, which is a complete identification of the medical order and its administration schedule. Below that, a screen display area 802 permits selection of a blood sugar level. Button displays 804, 806 may be selected to indicate that the sugar level is too low or too high, respectively, to be measured. Button displays 808 and 810 may be touched to move a pointer 812 along a scale 814 until the pointer 812 points to a measured blood sugar level. Alternatively, a button display 816 may be touched to display a numeric keypad permitting a measured blood sugar level to be entered numerically. Further, button displays 819 and 820 may be used to enter whether the blood sugar level is not, or is, respectively, entered.

Figure 11M:
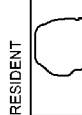
Figure 11N:
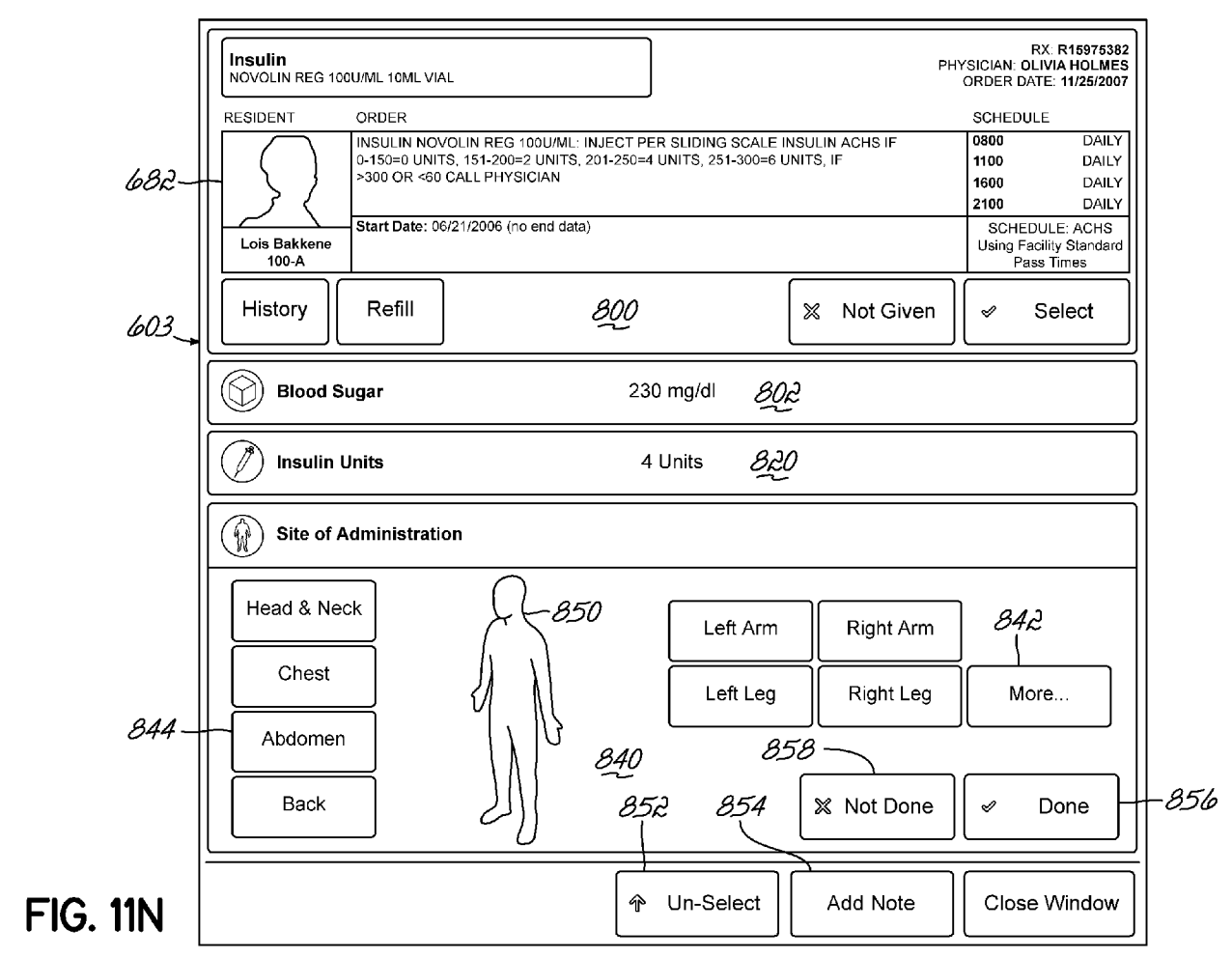

Upon selecting the done button display 818, a screen display 602 shown in FIG. 11M is presented. In this screen display, the area 802 displays the blood sugar level entered by the nurse; and the display area 820 has expanded to permit the entry of a number of insulin units administered. Again, button displays 822, 824, may be touched to move a pointer 826 with respect to a scale 828 until it is pointing to a number equal to the insulin units administered. Alternatively, a button display 830 may be selected to display a numeric key pad permitting the insulin units administered to be entered numerically. In addition, button displays, 832 and 834 may be used to indicate whether or not this activity is been completed. Upon selecting the done button display 832, a screen display 603 shown in FIG. 11N is presented. In screen display 603, the display area 820 has been reduced and displays the insulin units administered; and display 840 has expanded to provide anatomical selections for entering a site for administration of the insulin. A button display 842 may be selected to provide additional options for selecting a site of administration.

Figure 11O:
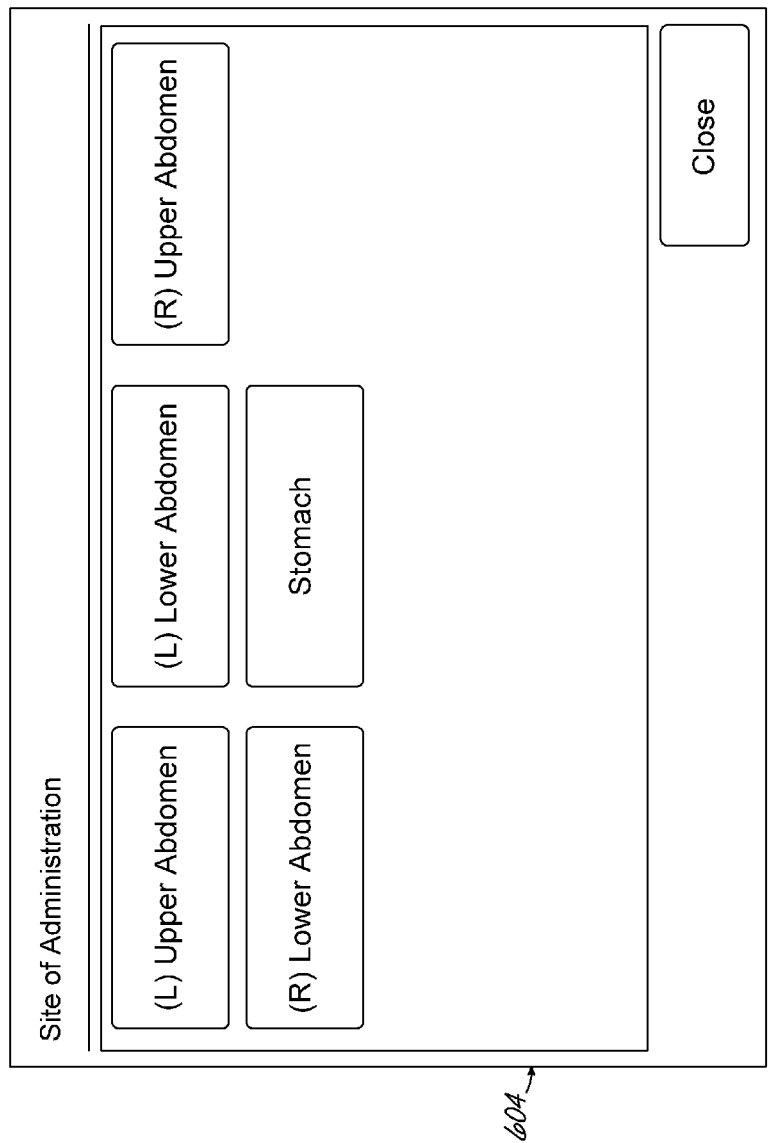
Figure 11P:
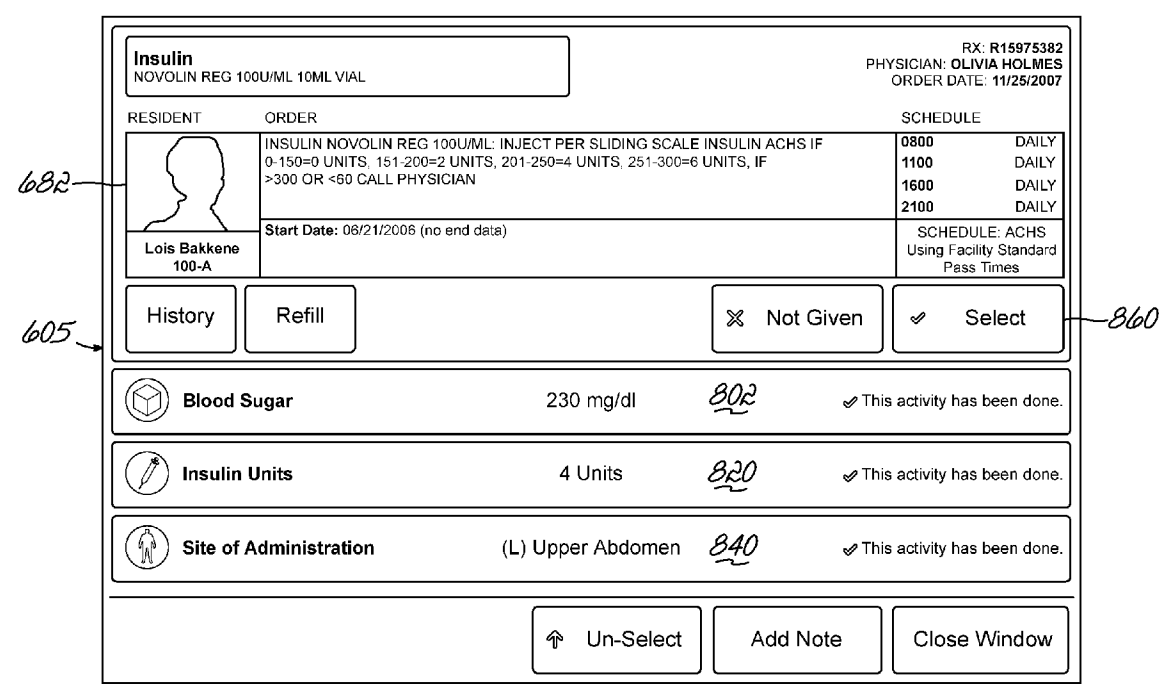

In addition, an abdomen button display 844 may be touched to provide a screen display 604 as shown in FIG. 11O in which various buttons displays relate to left or right sides of upper and lower portions of the abdomen. Upon selecting one of those button displays, the screen display 603 of FIG. 11N is presented. In some applications, upon selecting a particular administration site, an area representing that site may appear within a patient outline 850, thereby providing a visual representation of the site of administration selected. Once a site is selected, a button display 852 may be used to unselect the site. Further, button display 854 may be touched to provide additional notes relating to the administration of the insulin. Also, button displays 856 and 858 may be selected depending on whether a site of administration selection is completed. Upon selecting a done button display 856, the screen display 605 is presented as shown in FIG. 11P, in which the entries for blood sugar, insulin units administered, and the administration site are displayed and checked as being done.

Figure 11Q:
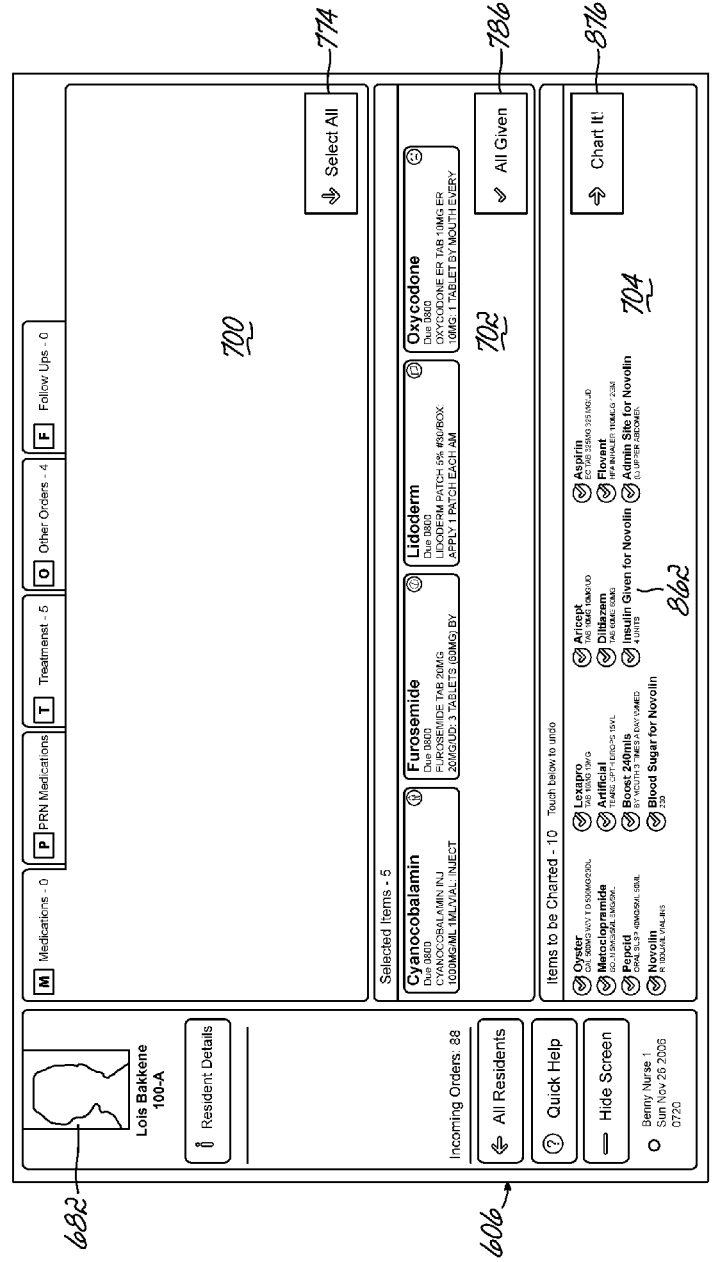

The given button display 860 may be touched to produce the display screen 606 shown in FIG. 11Q; and as shown at 862, the insulin order is now listed in the ready for charting display area 704. In a manner similar to that described with respect to insulin, the nurse performs the other activities required for charting of the medication orders remaining in the orders selected display area 702. After all activities for those remaining medication orders are completed, all of the ordered medications will then be listed in the ready for charting display area 704; and they are ready to be electronically charted.

Figure 11R:
Figure 11S:
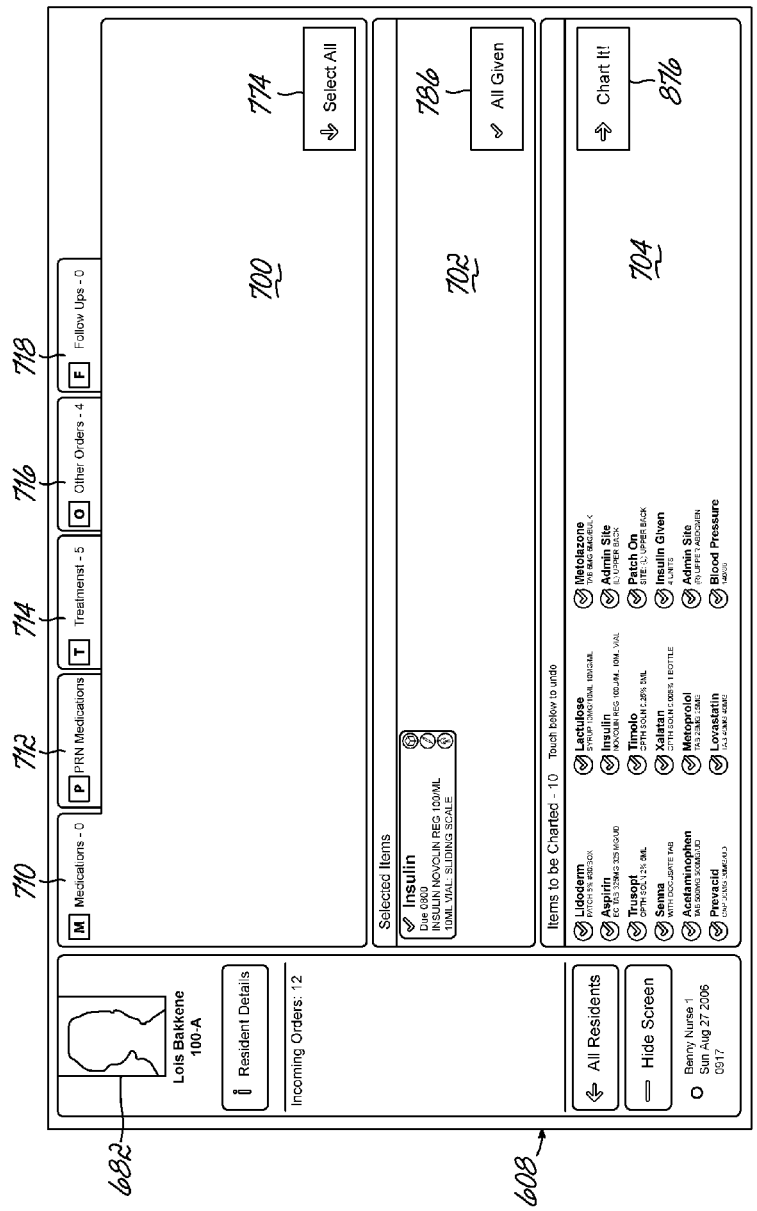

At this time, the nurse may review all of the data contained in the ready for charting display area 704 for accuracy. If any inaccuracy is found, the nurse simply touches the screen anywhere in the display area 704; and a screen display 607 shown in FIG. 11R is presented. Any medical order can be removed from the ready to chart display area by selecting a respective remove button display, for example, a remove button display 870 associated with insulin. After touching the remove button display 870 and the close button display 872, screen display 608 shown in FIG. 11S is presented. In that screen display, the medical order for insulin has been removed from the ready for charting display area 704 and has been returned to the orders selected display area 702. In a manner as previous described, the additional activities associated with the administration of insulin can be reviewed, and the entered values revised so that they are correct. Insulin can then again be selected as given, so that it is again listed in the ready to chart display area 704 as shown in FIG. 11Q.

After all medications have been administered and all additional activities completed, a chart it button display 876 may then be touched; and all of the data associated with the medication orders in the ready to chart display area 704 are logged to an electronic record of the eMAR that is stored in the database 34. The nurse is then returned to an all residents screen display 609 as shown by in FIG. 11T. At this point, the M tag for medications due that was associated with this resident photo 682 in FIG. 11E no longer appears with the resident photo in 682 in FIG. 11T.

Figure 11T:
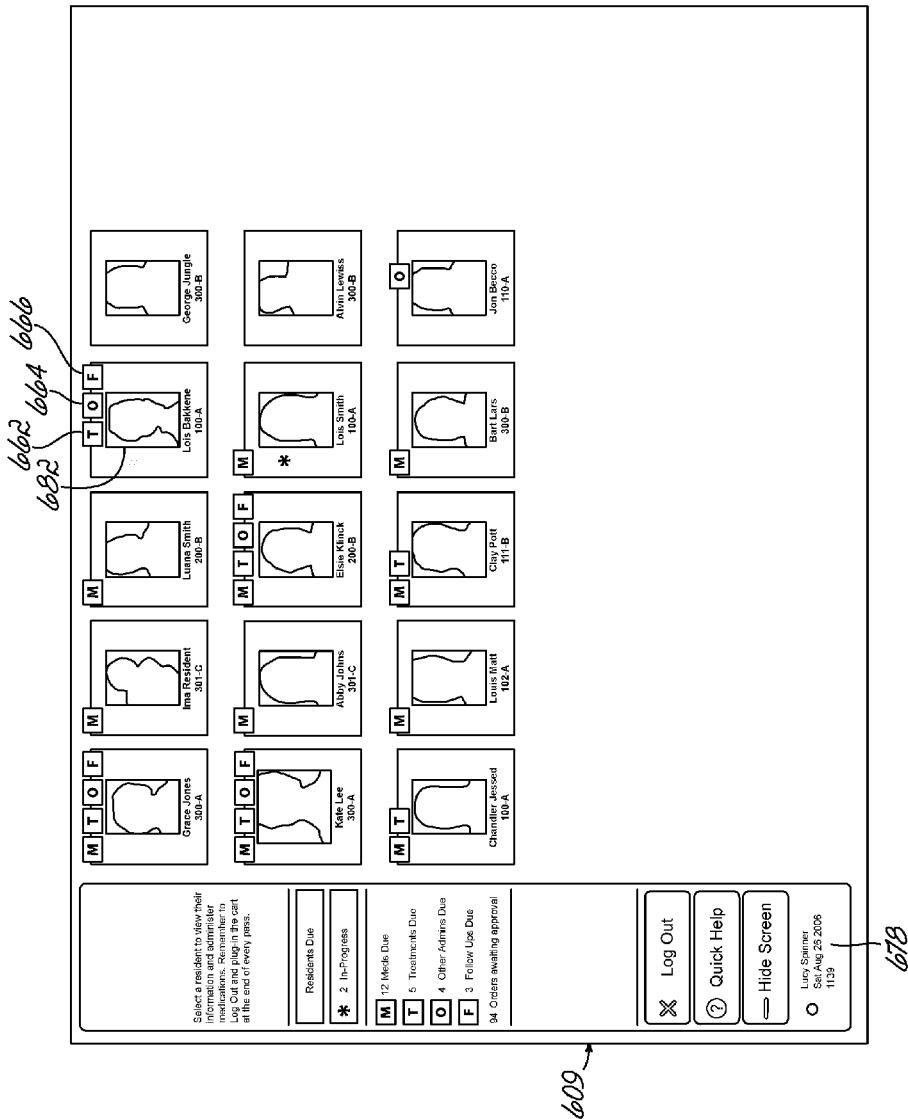

As shown in FIG. 11T, other orders for treatments, other orders and follow ups are also due for patient in resident photo 682. The nurse may choose to administer ones of those orders due depending on what is available on the medications cart that is being used. For example, the nurse could probably administer PRN medications if prescribed as shown in the screen display 595 of FIG. 11F. Otherwise, a nurse using a treatment cart will have to administer the treatment, other and followup orders due. In a manner as described above, the nurse may select medications due for other residents. In a manner similar to that previously described, other administrations are first selected at which time they automatically move to the selected area 702. Thereafter, the administrations are given and recorded using screens similar to that shown in FIGS. 11L-11P. After the other administrations are marked as given they are moved to the ready for charting area 704, where they can be reviewed prior to the charted touch button 876 being selected, which creates a permanent electronic chart of the other administration. Such other charting activities include but not limited to blood pressure, pulse rate, blood oxygen level, respiration, weight, pain assessment, intervention, lung sounds, PRN administration, PRN follow up, oral supplements and other activities required for medical care.

Referring to FIG. 11J, a feature of the invention is that activity tags 780 associated with the insulin order touch button 735 are automatically generated within the interface adaptor 40 ETL rules shown in FIG. 1. By requiring a pharmacy to utilize XML and data definitions, an example of which is shown and described with respect to FIGS. 3A-3I, an order, such as an insulin injection administration, can be readily searched for and identified. Further prescribed activities associated with that administration, such as recording the blood sugar level, insulin units administered and site may also be retrieved and stored. Those administration activities can then be automatically applied to the insulin order touch button 735 as respective tags 780 by the cart computer 26 in the process of creating the screen display 599 of FIG. 11J. Alternatively, the tags may be selected by a nurse at the nurses' station computer 50 in the process of reviewing and accepting the electronic insulin medication order when received from the pharmacy.

Figure 4C:
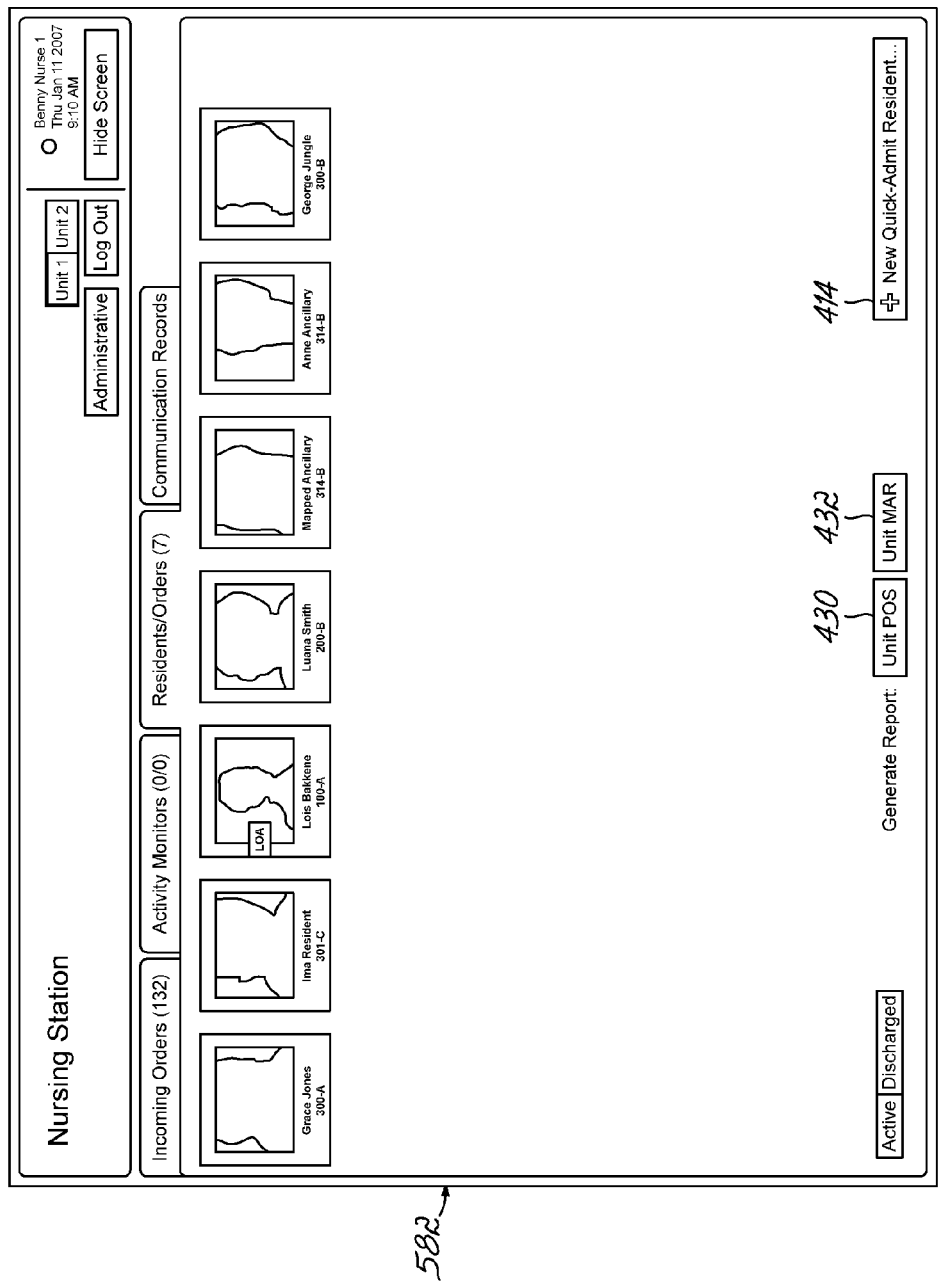
Figure 4D:
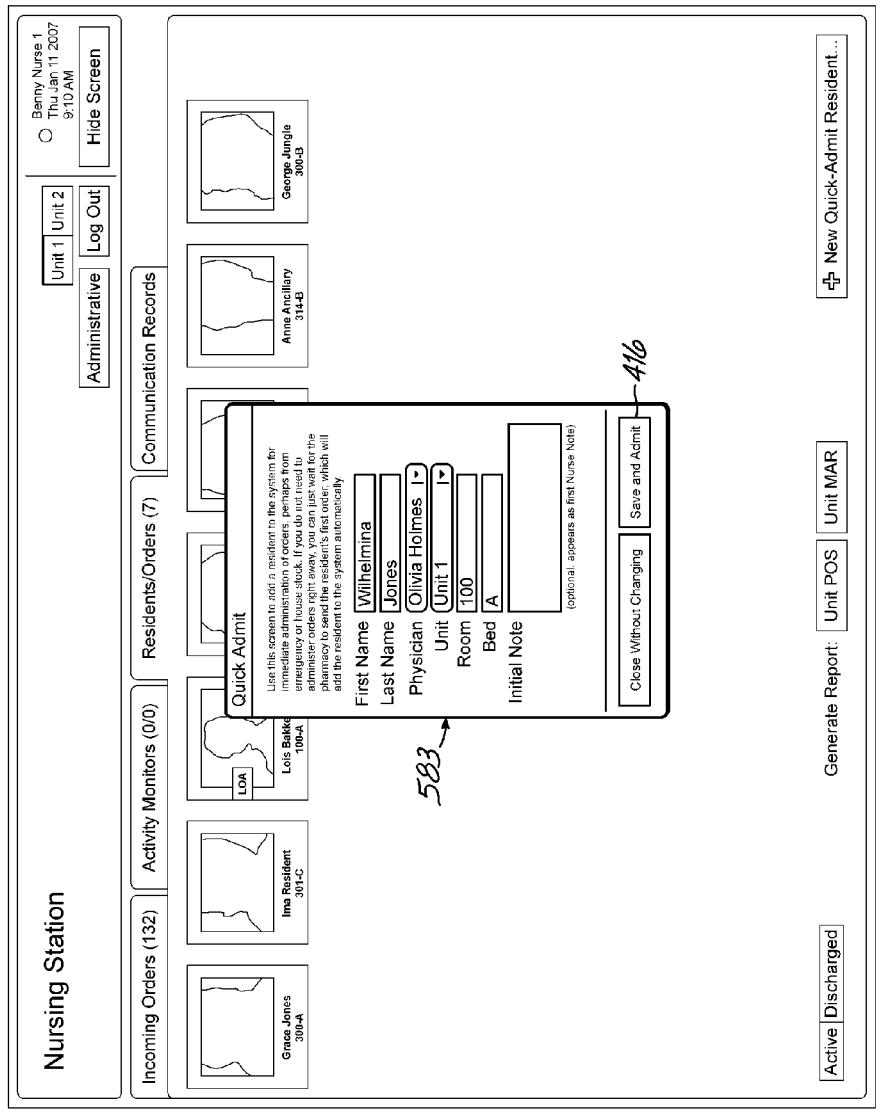
Figure 4E:
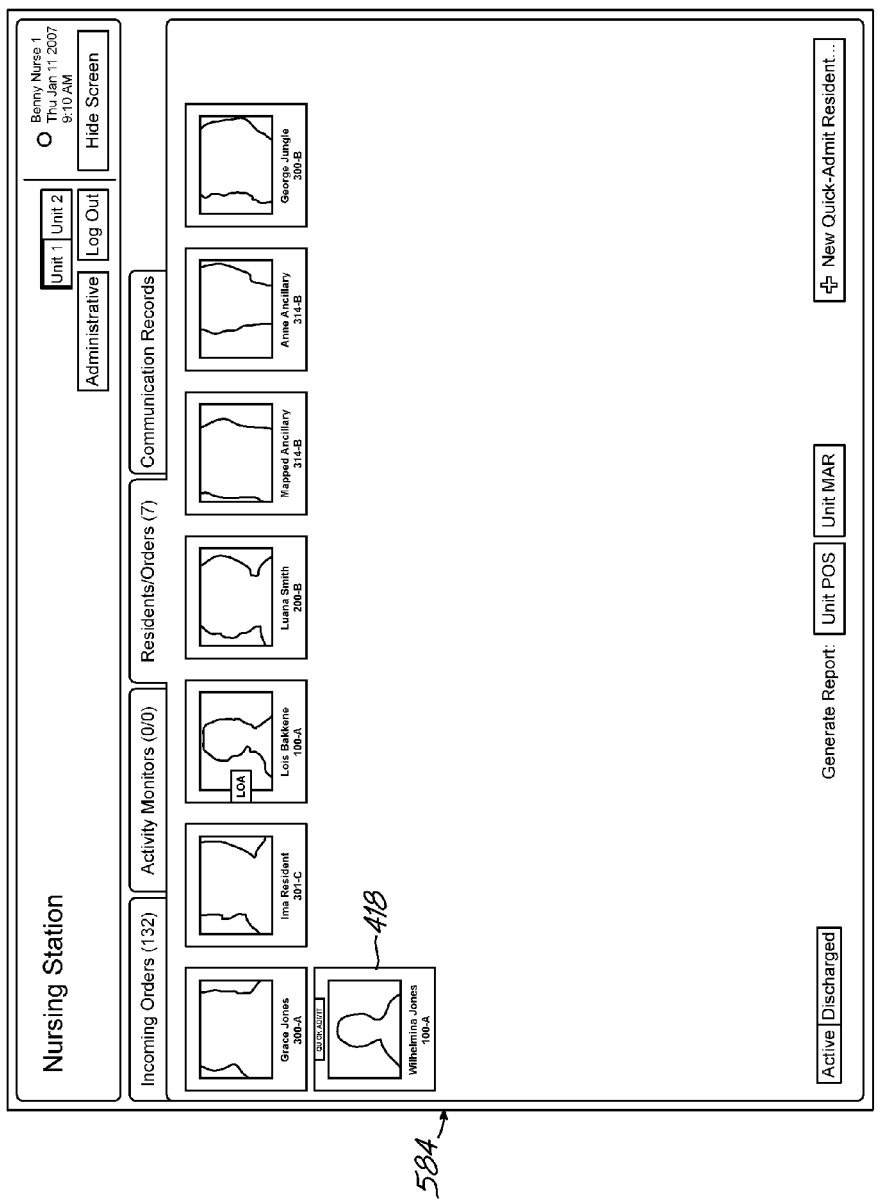

The medical care administration system 20 has a further capability of handling nonroutine after hours or emergency medication orders. Situations may arise where a resident requires a medication, and there is no time to process the medication order through the pharmacy or the pharmacy may be closed. Referring to FIG. 2, in those situations, the nurses' station computer 50 has an optional order entry capability that may be utilized by a nurse. For example, a new resident may be admitted and entered into the system when the pharmacy is closed. To do that, a nurse logs into the nurses' station computer 50 and a screen display 580 of FIG. 4A is produced. The nurse may then select a residents button display 412 and a screen display 582 of FIG. 4C is produced. The nurse then selects a new quick admit button display 414, and the nurses' station computer 50 provides screen window display 583 shown in FIG. 4D. The nurse then uses a keyboard with the nurses' station computer to enter the new resident's name, physician and room and bed location and selects the save and admit button display 416. A revised residents screen display 584 of FIG. 4E shows a display of the temporarily resident record just saved. The nurses' station computer 50 may be used to enter other data and/or a photograph. However, the resident record is a temporary one and will be replaced when the pharmacy is open and a real resident account is created within the pharmacy. Upon being saved with the button display 416, the temporary resident record is immediately transmitted to the application computer 30, which enters it into the database 34, pushes it down to the cart computer 26 and initiates an electronic facsimile of the temporary admission to the pharmacy 22.

Figure 4F:
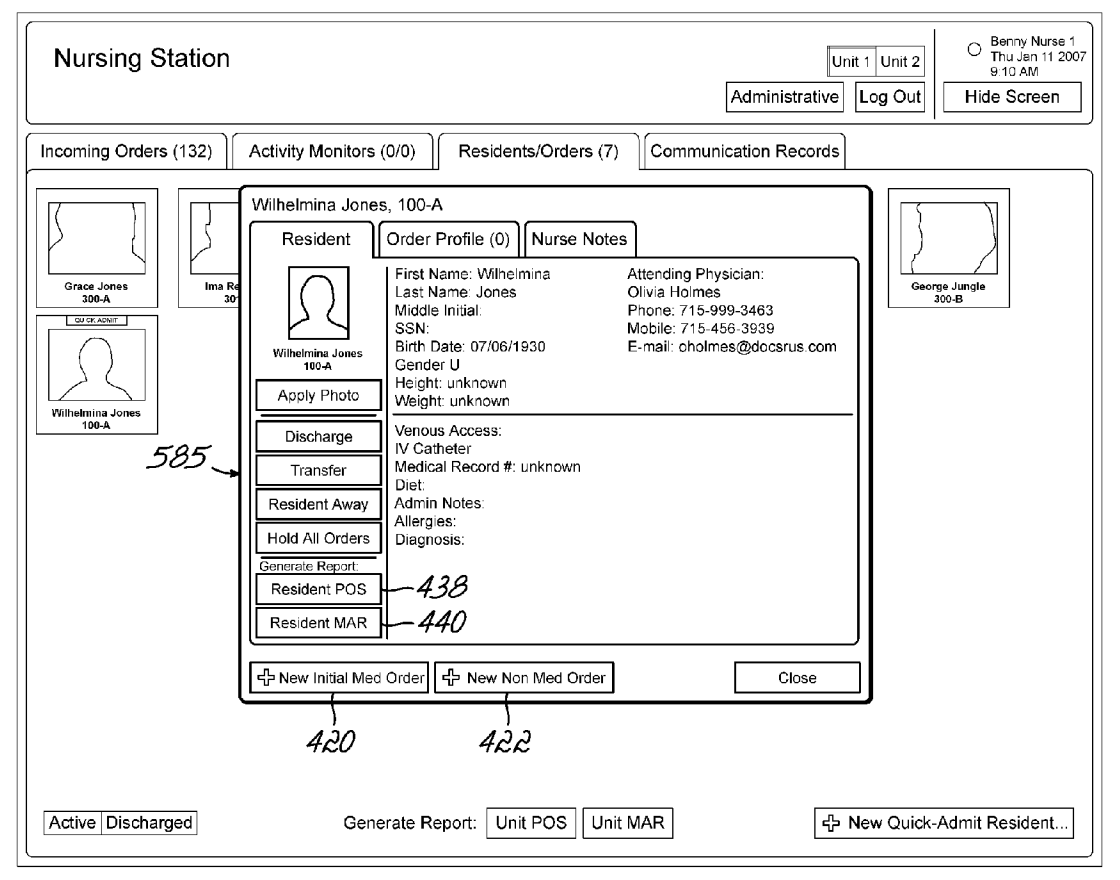
Figure 4G:
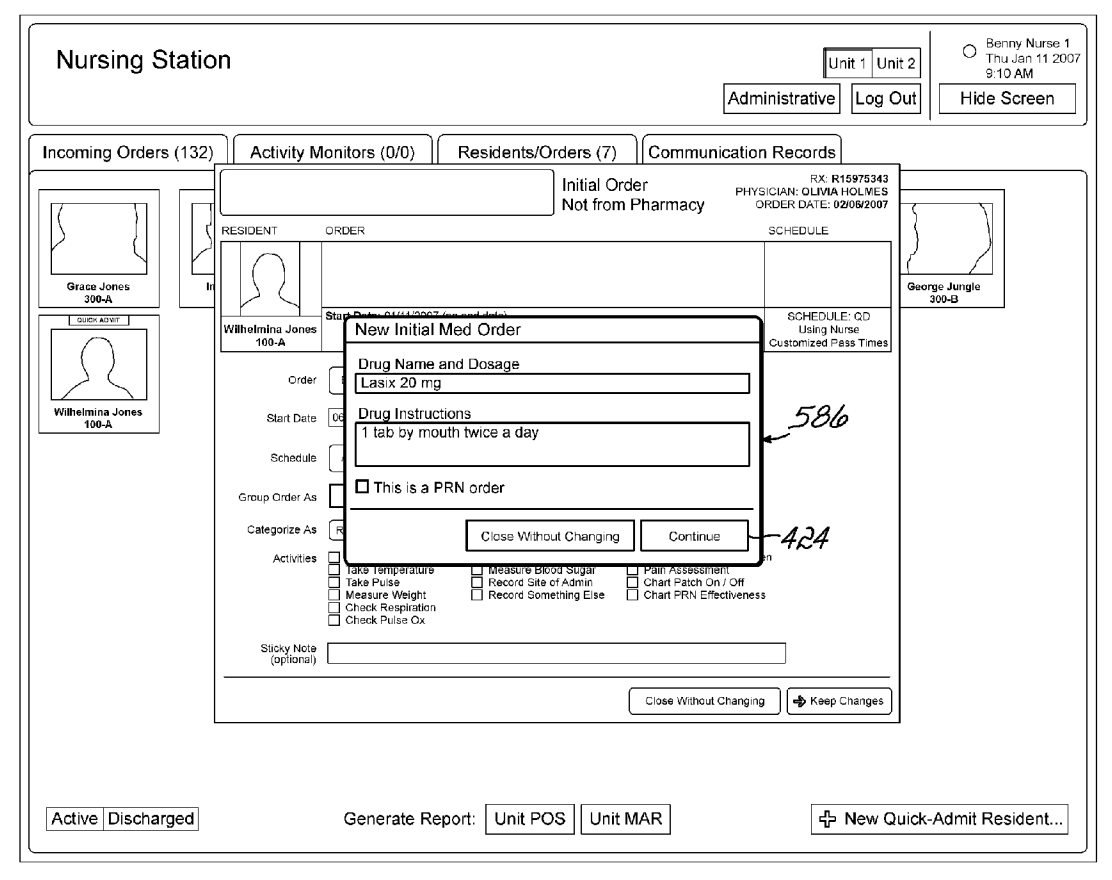
Figure 4H:
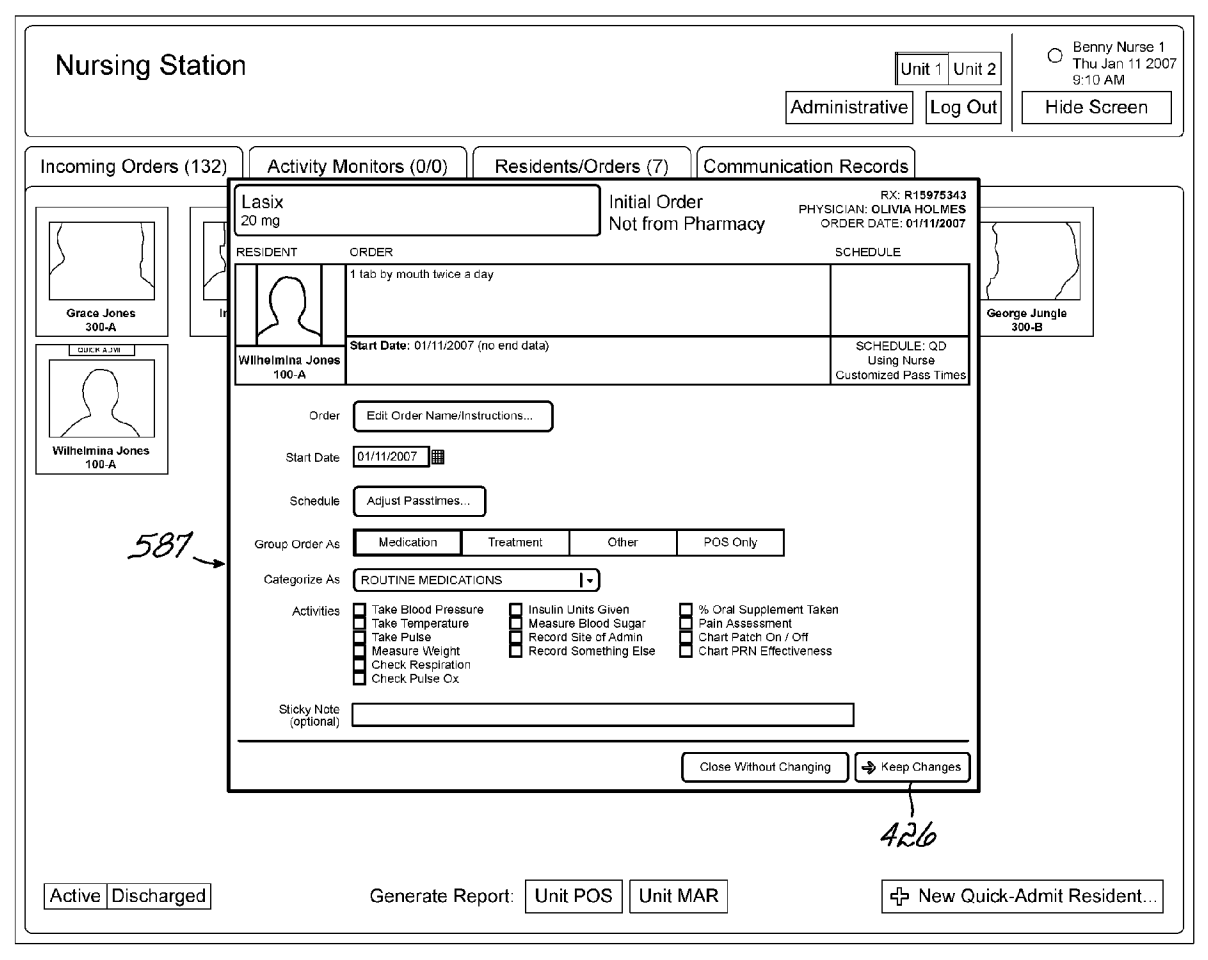
Figure 4I:
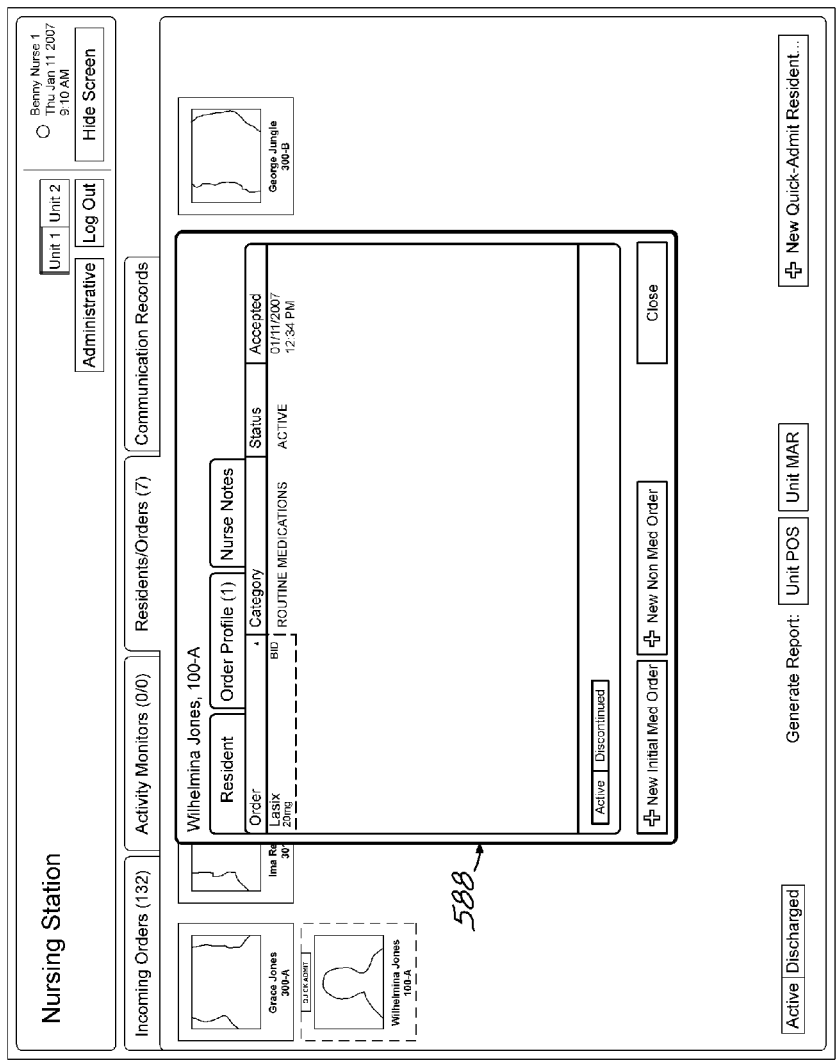

If it is desired to enter an new initial medical care order for the temporarily admitted resident, the nurse selects the display 418 and a window display 585 as shown in FIG. 4F is produced. The appropriate new initial med order button display 420 or the new initial non med order button display 422 may be selected. If the new initial med order button display is selected, a screen window display 586 as shown in FIG. 4G is provided; and the medication name, dosage and administration instructions may be entered using the keyboard. Upon selecting the continue button display 424, a screen display 587 as shown in FIG. 4H is presented, which is similar to screen display 581 of FIG. 4B, and allows the nurse to enter other information relating to the medication and its administration. When finished, the nurse selects the accept order button display 426; and a screen window display 588 of FIG. 4I is presented in association with the temporarily admitted resident. The dashed line around the medication name indicates that it is a temporary order. Upon being accepted, the temporary order data is sent from the nurses' station computer 50 to the application server 30, stored in the database 34 and transmitted to the cart computer 26. All temporary medication orders are also sent by electronic facsimile to the pharmacy 22. Temporary nonmedication orders are only sent to the pharmacy 22 if the pharmacy practice is to maintain them for record keeping purposes.

Subsequently, a physician may review the temporary medication order and issue a written order that is the same or different; and the written order is processed as earlier described herein. When the written order is subsequently accepted at the nurses' station computer 50 as described with respect to FIGS. 4A and 4B, it replaces the temporary order in the displays of the nurses' station computer 50 and the cart computer 26. Administration of a temporary medication or nonmedication order at the cart computer 26 is substantially identical to the previously described administration and charting processes. Thus, the medical care administration system 20 has the capability of sending medical care orders to a pharmacy either by faxing a written order from a physician in accordance with accepted practices or electronically creating an order at the nurses' station computer 50 that is then faxed to the pharmacy by the application server 30.

The medical care administration system 20 maintains data in the database 34 that may be used to print any reports that may required. For example, referring to FIG. 4A, upon selecting a report button display 436, further screen displays are provided that permit a user to print a late charting report, a login/logout report, a medication charting report by nurse, a medication charting summary report, a medication charting summary five minute rollup report and a missed charting report. Further, referring to FIG. 4E, upon selecting one of the residents, a residents detail screen display 585 is provided as shown in FIG. 4F. By selecting the resident MAR button display 440, a medical administration report may be printed for the resident for any month selected by the user. Similarly, the resident POS button display 438 may be selected to print a physician order sheet for the resident. In addition, referring to FIG. 4C, a unit POS button display 430 may be selected if it is desired to print a physician order sheet for all of the residents in a unit shown on the screen display 482. Similarly, a unit MAR button display 432 may be used to print a medication administration report for all of the residents in the unit.

An advantage of the medical care administration system 20 described herein is that it very accurately and reliably identifies all medical care orders that are due for administration. Further, the system 20 has a very high dynamic response to changes to the medical care order regardless of the origin of the changes. A further advantage is that large processing power and lead times are not required in order to calculate and recalculate when administrations are due. Therefore, at different times or the same times, the cart computer 26, nurses' station computer 50 and application server 30 may all independently perform the administrations due calculations for all of the medical care orders in the medical care facility 24. As described, the cart computers 26 calculate when administrations are due to present a care giver current information for an administration of a medical care order. If an administration is late, it may be presented on the cart computer screen as a late administration. The nurses's station computer may also independently calculate when administrations are due to identify administrations that are late. Those late administrations are identified on a late-activity monitor, so that supervisors can react appropriately. Thus, the results of the calculations by the nurses' station computer 50 are used locally in the medical care facility 24 and are not transferred to the application server 30.

The application server 30 may also independently calculate when administrations due in order to generate paper charts that may be used for charting in special circumstances, for example, during an extended power failure in the geographic area of the medical care facility. The application server 30 may also calculate when administrations due within various time periods in order to optimize data distribution. The memory available in different cart computers may vary significantly; and the application server should download only that data that respective cart computes can properly store and process.

Figure 12:
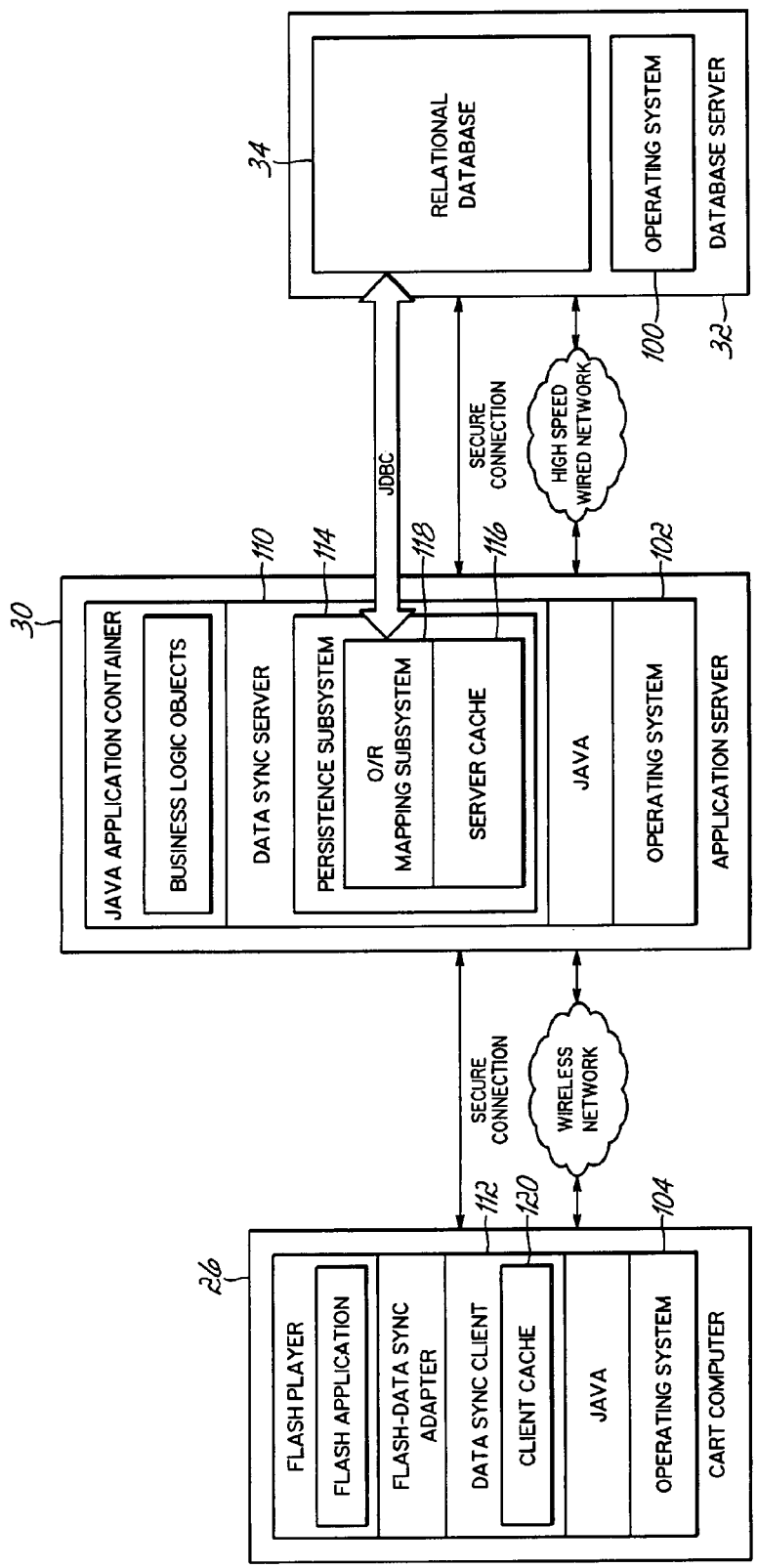
FIG. 12 is an exemplary representation of components within the high level architecture of the medical care administration system illustrated in FIG. 1.

The transfer of data between the database 34 and the cart computer 26 via the application server 30 may be accomplished using known techniques. For example, referring to FIG. 12, in one exemplary embodiment, the database server 32, application server 30 and cart computer 26 have respective core operating systems 100, 102, 104. The application server 30 and cart computer 26 have, respectively, a data synchronization server 110 and data synchronization client processor 112. Within the data synchronization server 110, a persistence subsystem 114 has a server cache 116 and a object/relational mapping subsystem 118. The object/relational mapping subsystem 118 may be implemented using a high performance object relational persistence and query service, for example, HIBERNATE software that is commercially available from Red Hat Americas of Raleigh, N.C. The data synchronization client processor 112 has a client cache 120. An interface with the database 34 is provided by Java Database Connectivity ("JDBC") application programming interface that is a commercially available standard SQL database access interface.

The data synchronization server 110 and data synchronization client 112 are operative to provide a synchronization of data between the server cache 116 and the client cache 120. Thus, the server cache 116 and client cache 120 should always contain substantially current and identical data. However, data in the database 34 may change based on inputs from the pharmacy, various cart computers 26-26n, and/or the nurses' station computer 50, which affects the administrations due calculations. In that situation, the data synchronization server 110 identifies that changed data and causes the changed data to be moved to the server cache 116; after which, it is immediately transferred to the client cache 120. Thus, the changed data is quickly made available to the cart computer 26 and its administrations due calculations. In other situations, the charting of administrations with the cart computer 26 also generates new data that affects the administrations due calculations and should be input to the database 34. Therefore, the data synchronization client 112 is effective to quickly transfer that new data from the client cache 120 to the server cache 116; and the data synchronization server 114 is operative to immediately transfer the new data into the database 34. The changed data is then immediately pushed back out to the cart computers 26 and nurses' station computers 50.

By maintaining the data in the server and client caches 116, 120 synchronized, the cart computer 26 is capable of executing the administrations due calculations with current data even if there is a loss of connectivity with one or more of the wireless networks 46, 48. In a known manner, the data synchronization server 110 and data synchronization client 112 are operative to detect the loss of connectivity, keep track of what data was in their respective caches 116, 120 when the loss connectivity occurred and what data in their respective caches 116, 120 changed during the loss of connectivity. Further, when connectivity is again established, the data synchronization server 110 and data synchronization client 112 are operative to resync their respective caches 116, 120, so that current data is contained in the database 34 and available to the cart computer 26 for performing the administrations due calculations. The transfer of data between the relational database 34 and the nurses' station computer 50 is substantially identical to that described with respect to cart computer 26. The nurses' station computer 50 also has a data synchronization client and client cache substantially similar respectively to the data synchronization client 112 and client cache 120 in the cart computer 26.

While the present invention has been illustrated by the description of an exemplary embodiment thereof, and while the embodiment has been described in considerable detail, it is not intended to restrict or in any way limit the scope of the appended claims to such detail. Additional advantages and modifications will readily appear to those skilled in the art. For example, referring to FIG. 1, the medical care administration system 20 described herein may be used with only one medical care facility 24 that has only one nurses' station computer 50 and only one cart computer 26 and orders from only one pharmacy 22. Further, only one application server 30 and only one database server 32 and their respective interfaces 36, 40, 42, 44 may be used with a database 34. In different exemplary embodiments the application server 30 and its interfaces, the database server 32 and its interfaces and the database 34 may be have different geographic locations with respect to the medical care facility 24 and pharmacy 22. In one embodiment, they may be located at a common location in a data center 72. In some embodiments, the data center 72 may be geographically remote from the medical care facility 24 and the pharmacy 22. In other embodiments, the data center 72 may be geographically near the medical care facility 24 or the pharmacy 22. In still further embodiments, pharmacy 22, the medical care facility 24 and data center 72 may have a geographically common location.

In yet other embodiments, the medical care administration system may be used with multiple pharmacies 22-22*n* and/or multiple medical care facilities 24-24*n* that have multiple nurses' station computers 50-50*n* and multiple cart computers 26-26*n*. Further, the data center 72 may have multiple application servers 30-30*n*, multiple database servers 32-32*n* with respective multiple interfaces 36-36*n*, 40-40*n*, 42-42*n*, 30-30*n*. In such embodiments containing multiple components, the medical care administration system 20 operates substantially similarly to that described herein with respect a system having only one of each component. In multiple component systems, an application server 30, database servers 32 and their respective interfaces may be dedicated to a single medical care facility 24. However, the administrations due calculations may be run independently by a grid of all of the cart computers 26-26*n* and all of the nurses' station computers 50-50*n* as well as the application server 30. Further, new or changed data may result from any one of the cart computer calculations or an input from any of the nurses' station computers; and the application server 30 must keep track of the data changes, the source of the data changes and decide how to update the database. In different embodiments, different known algorithms and techniques may be used to decide what data to accept and store in the database 34, for example, a pessimistic locking algorithm, an optimistic locking algorithm or other comparable algorithm.

The invention in its broader aspects is therefore not limited to the specific details, representative apparatus and methods and illustrative examples shown and described. Accordingly, departures may be made from such details without departing from the scope or spirit of Applicants' general inventive concept.

What is claimed is:

1. A method for facilitating an administration of medical care comprising:
    receiving an order for medical care using an application server;
    storing, in a relational database of an administration computer which includes each order for medical care data relating to an identity of a person which is to receive the medical care, an identity of one of a pharmaceutical and a treatment, an order start date, a frequency of administration, an administration interval start time, an administration interval stop time and a duration of the order for medical care, the relational database being in electrical communication with the application server, the data permitting a determination, for each order, of a plurality of administration windows during which medical care in the order is to be administered over the duration of the order;
    synchronizing the relational database of the administration computer in response to establishing connectivity to a data synchronization server; and
    calculating, with the administration computer and for the person which is to receive the medical care, a current administration requirement of the medical care using data from the relational database, the calculating being repeatedly performed at each administration interval start time.

2. The method of claim 1 further comprising:
    producing the order in written form for medical care within a medical care facility;
    providing the written order for medical care to a pharmacy by facsimile transmission;
    converting the written order for medical care to an electronic pharmacy order for medical care;
    receiving an electronic pharmacy order for medical care with the application server, the electronic pharmacy order being created in response to the written order;
    storing in the relational database first data that may be used to generate an electronic administration record of the medical care order in response to receiving the electronic pharmacy order;
    transmitting the first data to a computer in the medical care facility;
    comparing the first data with the written order for medical care;
    accepting the first data as accurately representing the written order for medical care.

3. The method of claim 2 wherein after the step of receiving the electronic pharmacy order, the method further comprises transforming with the application server the electronic pharmacy order for medical care into the first data having a normative format of standard definitions.

4. The method of claim 3 wherein after the accepting step, the method further comprises:
providing the first data to an administration cart computer; and
generating with the administration cart computer second data relating to a charting of an administration of the medical care order;
providing the second data to the application server; and
storing the second data in the relational database.

5. The method of claim 4 wherein the method further comprises:
generating an electronic administration record in response to the first data.

6. The method of claim 4 wherein the method further comprises:
generating an electronic administrative record in response to the first data and the second data.

7. The method of claim 2 wherein all data relating to the written medical care order is provided to the pharmacy by only facsimile transmission.

8. The method of claim 2 wherein all data relating to the electronic pharmacy order is provided only from the pharmacy to the application server.

9. The method of claim 2 wherein no data relating to the written medical care order is provided from the application server to the pharmacy.

10. The method of claim 1 further comprising:
producing the medical care order in written form within a medical care facility;
providing the written medical care order to a pharmacy by facsimile transmission;
generating an electronic pharmacy medical care order in response to the written medical care order;
receiving the electronic pharmacy medical care order with an application server;
generating in response to a user input a first screen display on a first computer in the medical care facility, the first display permitting a selection of a temporary order entry relating to one of a medication order, a non-medication order and a new admittance;
generating, in response to an input selecting the temporary order entry display a series of further screen displays permitting an entry of data relating the temporary order entry; and
generating a further display permitting an acceptance of the temporary order entry.

11. The method of claim 10 wherein in response to an input selecting the acceptance of the temporary order entry, the method further comprises:
transmitting the data relating to the temporary order entry to the application server;
storing the data relating to the temporary order entry in the relational database; and
transmitting the data relating to the temporary order entry to a second computer in the medical care facility operable during an administration of the medical care order.

12. The method of claim 11 further comprising:
transmitting a facsimile copy of the data relating to the temporary order entry to the pharmacy.

13. The method of claim 12 further comprising:
producing a second written medical care order within the medical care facility relating to the temporary order entry;
providing the second written medical care order to a pharmacy by facsimile transmission;
generating an electronic second pharmacy medical care order in response to the second written medical care order;
receiving the second electronic pharmacy medical care order with the application server;
storing in the relational database second data that may be used to generate an electronic administration record of the second written medical care order in response to receiving the second electronic pharmacy medical care order;
generating a screen display of the first computer permitting an acceptance of the second data representing the second written medical care order; and
transmitting the second data to the second computer to replace the data relating to the temporary order entry.

14. The method of claim 1 further comprising:
providing with a services oriented architecture one message format for the medical care order and data definitions for the one message format using a web services description language;
creating with the administration computer associated with a pharmacy an electronic pharmacy order for the medical care order using the one message format and the data definitions;
receiving the electronic pharmacy order for the medical care order with an application server;
transforming with the application server the electronic pharmacy order for the medical care order to first data in a normative format of definitions derived from the one message format and the data definitions; and
storing the first data in the relational database, the first data being usable to generate an associated electronic administration record.

15. The method of claim 14 further comprising providing with the services oriented architecture message formats for one of a medication order, a non-medication order, a discontinue and void order, a resident demographics order, a physician demographics order and an administration override order.

16. The method of claim 15 further comprising providing with the services oriented architecture message formats for each of a medication order, a non-medication order, a discontinue and void order, a resident demographics order, a physician demographics order and an administration override order.

17. The method of claim 1 further comprising:
determining, in response to storing the data for the medical care order, start and stop times of a first administration interval with respect to the order start date;
calculating a number of start times of respective administration intervals occurring between the order start date and a first time after storing the data for the order for medical care;
calculating a number of stop times of respective administration intervals occurring between the order start date and the first time;
comparing the number of start times to the number of stop times; and
determining that the medical care order is due for administration at the first time in response to the number of start times not being substantially equal to the number of stop times.

18. The method of claim 17 further comprising providing a human perceptible output in response to determining that the order for medical care is due for administration.

19. The method of claim 17 further comprising determining that the order for medical care is not due for administration at the first time in response to the number of start times being substantially equal to the number of stop times.

20. The method of claim 17 further comprising:
storing data representing a change in the order for medical care; and
iterating the steps following the storing in a database step in response to storing the data representing the change in the order for medical care.

21. The method of claim 17 further comprising iterating the steps at periodic intervals after the first time.

22. The method of claim 21 wherein the periodic intervals are variable.

23. The method of claim 21 wherein the periodic intervals are fixed.

24. The method of claim 21 wherein the periodic intervals are measured in one of seconds, minutes and hours.

25. The method of claim 1 wherein the method further comprises:
storing in an orders table for each order for medical care data relating to an order identity, a frequency of administration identity, an order start date, an identity of a person to receive a respective order for medical care, an identity of one of a pharmaceutical and a treatment, and other data relating to the order;
storing in a frequency elements table for each order identity data relating to a frequency element identity, and a frequency definition element identity;
storing in a frequency definition elements table for each frequency of administration identity data relating to a frequency definition element identity, an administration start time, an administration stop time and a repeat interval; and
storing in a frequency definition table data relating to each frequency of administration identity.

26. The method of claim 25 wherein the data relating to the repeat interval comprises data relating to a repeat interval as measured in hours.

27. The method of claim 25 wherein the data relating to the repeat interval comprises data relating to a repeat interval as measured in months.

28. The method of claim 25 further comprising assigning respective global universal identities to the order identity, the frequency of administration identity, the identity of a person to receive a respective order for medical care, the frequency element identity, and the frequency definition element identity, the respective global universal identities being used in different tables.

29. The method of claim 1 further comprising:
generating with the administration computer a first screen display identifying persons in the medical care facility currently requiring administrations of respective medical care orders;
generating with the administration computer and in response to a first person being selected from the first screen display, a second screen display having a display portion identifying the first person;
a first display area identifying medical care orders currently due for administration to the first person,
a first button display for selecting a first medical care order,
a second display area identifying medical care orders selected for administration, the second display area identifying the first medical care order in response to the first button display being selected, and upon the first medical care order being identified in the second display area, the first medical care order ceases to be identified in the first display area,
a second button display for selecting the first medical care order as being administered,
a third display area identifying medical care orders ready for charting, the third display area identifying the first medical care order in response to the second button display being selected, and upon the first medical care order being identified in the third display area, it ceases to be identified in the second display area, and
a third button display for updating electronic administration records for respective medical care orders identified in the third display area.

30. An apparatus for providing data used to generate an electronic administration record of a medical care order created in a medical care facility comprising:
a facsimile machine in the medical care facility adapted to transmit by facsimile copy a written medical care order to a pharmacy;
an application server adapted to receive an electronic pharmacy medical care order corresponding to the written medical care order;
a database server connectable to the application server and comprising a relational database adapted to store first data adapted to correspond to the electronic pharmacy medical care order, the first data information relating to medical care orders, and for each medical care order, the first data relating to an identity of a person to receive a respective medical care order, an identity of one of a medication and a treatment, an order start date, a frequency of administration, an administration interval start time, an administration interval stop time and a duration of the order for medical care;
a wireless network connectable to the applications server; and
an administration computer connectable to the application server via the wireless network for receiving the first data from, and providing second data to, the relational database and synchronizing the relational database of the administration computer in response to reestablishing connectivity to a data synchronization server,
the administration computer calculating, for the person which is to receive the medical care, a current administration requirement of the medical care using data from the relational database, the calculating being repeatedly performed at each administration interval start time.

31. The apparatus of claim 30 further comprising:
a display screen in electronic communication with the administration computer and being operable to present on the display screen a first display permitting a comparison between the first data and the written order for medical care, and
a second display permitting an acceptance of the first data as accurately representing the written order for medical care.

32. The apparatus of claim 30 further comprising:
a pharmacy computer adapted to store an electronic pharmacy order for the medical care order;
wherein the application server is adapted to receive the electronic pharmacy order from the pharmacy computer;
wherein the relational database is in electronic communications with the application server and adapted to store first data corresponding to the electronic pharmacy order;
a display screen in electronic communication with the administration computer and being operable to present on the display screen a first display permitting a selection of a temporary order entry relating to one of a medication order, a non-medication order and a new admittance;

a series of further displays permitting an entry of data relating the temporary order entry, and a further display permitting an acceptance of the temporary order entry.

33. The apparatus of claim 30 further comprising:

a website accessible by the pharmacy for storing a message format for the medical care order and data definitions for the message format using a web services description language; and first data generated by the application server having a normative format of definitions derived from the one message format and the data definitions.

34. The apparatus of claim 30 wherein the administration computer repeatedly executes the independent calculations for each respective medical care order over a duration starting before an order start and ending at a respective order end date.

35. The apparatus of claim 30 wherein the relational database comprises:

an orders table for storing for each medical care order data relating to an order identity, a frequency of administration identity, an order start date, an identity of a person to receive a respective medical care order, an identity of one of a pharmaceutical and a treatment, and other data relating to the respective medical care order;

a frequency elements table for storing for each order identity data relating to a frequency element identity, and a frequency definition element identity;

a frequency definition elements table for storing for each frequency of administration identity data relating to a frequency definition element identity, an administration start time, an administration stop time and a repeat interval; and a frequency definition table for storing data relating to each frequency of administration identity.

36. The apparatus of claim 35 wherein the data relating to the repeat interval comprises data relating to a repeat interval as measured in hours.

37. The apparatus of claim 36 wherein the data relating to the repeat interval comprises data relating to a repeat interval as measured in months.

38. The apparatus of claim 37 wherein the data relating to the order identity, the frequency of administration identity, the identity of a person to receive a respective medical care order, the frequency element identity, the frequency definition element identity are data having a global universal identity.

39. The apparatus of claim 38 wherein at least one of an identity of a person to receive a respective medical care order, an order identity, a frequency of administration identity, a frequency element identity and a frequency definition element identity are assigned a global universal identification.

40. The apparatus of claim 30 further comprising:

a first screen display generated by the administration computer and identifying persons in the medical care facility currently requiring administrations of respective medical care orders, a second screen display in response to an input provided by a first person being selected from the first screen display, the second screen display comprising a display portion identifying the first person;

a first display area identifying medical care orders currently due for administration to the first person, a first button display for selecting a first medical care order for administration, a second display area identifying medical care orders selected for administration, the second display area identifying the first medical care order in response to the first button display being selected, and upon the first medical care order being identified in the second display area, the first medical care order ceases to be identified in the first display area, a second button display for selecting the first medical care order as being administered, a third display area identifying medical care orders ready for charting, the third display area identifying the first medical care order in response to the second button display being selected, and upon the first medical care order being identified in the third display area, it ceases to be identified in the second display area, and a third button display for updating electronic administration records for respective medical care orders identified in the third display area.

41. The apparatus of claim 40 wherein the first button display is part of a display of one of the medical care orders identified in the first display area, and the first display button being effective to select the one of the medical care orders.

42. The apparatus of claim 41 wherein the first button display is part of the first display area, and the first display button being effective to select all of the medical care orders identified in the first display area.

* * * * *